United States Patent
Kotin et al.

(10) Patent No.: US 6,723,551 B2
(45) Date of Patent: Apr. 20, 2004

(54) PRODUCTION OF ADENO-ASSOCIATED VIRUS IN INSECT CELLS

(75) Inventors: Robert M. Kotin, Bethesda, MD (US); Masashi Urabe, Rockville, MD (US); Chuan-Tian Ding, Chevy Chase, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/216,870

(22) Filed: Aug. 13, 2002

(65) Prior Publication Data

US 2003/0148506 A1 Aug. 7, 2003

Related U.S. Application Data

(63) Continuation-in-part of application No. 09/986,618, filed on Nov. 9, 2001.

(51) Int. Cl.⁷ .......................... C12N 7/00; C12N 15/00; C12Q 1/70; C12P 21/06; C07H 21/04
(52) U.S. Cl. .......................... 435/235.1; 435/5; 435/6; 435/69.1; 435/69.7; 435/320.1; 536/23.72
(58) Field of Search .................... 435/5, 6, 69.1, 435/69.7, 320.1, 235.1; 536/23.72

(56) References Cited

U.S. PATENT DOCUMENTS

| | | |
|---|---|---|
| 5,387,484 A | 2/1995 | Doany |
| 5,688,676 A | 11/1997 | Zhou et al. |
| 5,691,176 A | 11/1997 | Lebkowski et al. |
| 5,741,683 A | 4/1998 | Zhou et al. |
| 6,156,303 A | 12/2000 | Russell et al. |
| 6,204,059 B1 | 3/2001 | Samulski et al. |
| 2001/0016355 A1 | 8/2001 | Samulski et al. |
| 2002/0081721 A1 | 6/2002 | Allen et al. |

FOREIGN PATENT DOCUMENTS

| | | |
|---|---|---|
| WO | WO 96/17947 A1 | 6/1996 |
| WO | WO 00/24916 A1 | 5/2000 |
| WO | WO 00/47757 A1 | 8/2000 |

OTHER PUBLICATIONS

An et al., *J. Gen. Virol.*, 80(pt. 4), 1009–1016 (1999).
Berns, K. I., "*Parvoviridae*: The Viruses and Their Replication," Chapter 69 in Fields Virology (3d Ed. 1996).
Bantel–Schaal et al., *J. Virol.*, 73(2), 939–947 (1999).
Brown et al., *J. Virol.*, 65(5), 2702–2706 (1991).
Chang et al., *J. Gen. Virol.*, 78(pt. 6), 1435–1439 (1997).
Chiorini. J. et al., *J. Virol.*, 71(9), 6823–6833 (1997).
Chiorini, J. et al., *J. Virol.*, 73(5), 4293–4298 (1999).
Chiorini, J. et al., *J. Virol.*, 73(2), 1309–1319 (1999).
Conway, J. et al., *Gene Thereapy* 6, 986–993 (1999).
Conway, J. et al., *J. Virol.*, 71(11), 8780–8789 (1997).
Davidson et al., *Proc. Natl. Acad. Sci. USA*, 97(7), 3428–3432 (2000).

(List continued on next page.)

*Primary Examiner*—Hankyel T. Park
(74) *Attorney, Agent, or Firm*—Leydig, Voit & Mayer, Ltd.

(57) ABSTRACT

A method of producing an adeno-associated virus (AAV) in an insect cell comprising (i) providing at least one insect cell-compatible vector comprising a first nucleotide sequence comprising at least one AAV ITR nucleotide sequence, a second nucleotide sequence containing an open reading frame encoding AAV VP1, VP2, and VP3 capsid proteins, a third nucleotide sequence comprising a Rep52 or a Rep40 coding sequence, and a fourth nucleotide sequence comprising a Rep78 or a Rep68 coding sequence, (ii) introducing the at least one insect cell-compatible vector into an insect cell, and (iii) maintaining the insect cell under conditions such that AAV is produced. Also provided are recombinant AAV made in accordance with the method, insect cell-compatible vectors, and insect cells comprising nucleotide sequences for production of AAV in an insect cell.

36 Claims, 10 Drawing Sheets

OTHER PUBLICATIONS

Ding, C., et al., *J. Virol.*, 76(*1*), 338–345 (2002).
Gao, G., et al., *Human Gene Therapy 9*, 2353–2362 (1998).
Grimm et al., *Hum. Gene Ther.*, 10(*15*), 2445–2450 (1999).
Hoque, M. et al., *J. Biochem. & Biophys.*, 266, 371–376 (1999).
Jennings et al., *Arthritis Res*, 3, 1 (2001).
King, J. et al., *Embo J.*, 20(*12*), 3282–3291 (2001).
Kogukegawa et al., *Biochim. Biophys. Acta, 1290*(*1*), 37–45 (1996).
McCarty, D. et al., *J. Virol.*, 68(*8*), 4988–4997 (1994).
Montross et al., *J. Virol.*, 65(*9*), 4991–4998 (1991).
Owens, R., *Virology, 184*, 14–22 (1991).
Palombo, F. et al., *J. Virol.*, 72(*6*), 5025–5034 (1998).
Qiao, C., et al., *J. Virol.*, 76(*4*), 1904–1913 (2002).
Ruffing, M. et al., *J. Virol.*, 66(*12*), 6922–6930 (1992).
Rutledge, E. et al., *J. Virol.*, 72(*1*), 309–319 (1998).
Samulski, R., *J. Virol.*, 63(*9*), 3822–3828 (1989).
Sandalon et al., *Virology, 237*(*2*), 414–421 (1997).
Smith, R. et al., *J. Virol.*, 71(*6*), 4461–4471 (1997).
Smith, R. et al., *J. Virol.*, 72(*6*), 4874–4881 (1998).
Smith, R. et al., *J. Virol.*, 74(*7*), 3122–3129 (2000).
Sollerbrant, K. et al., *J. Gen. Virol., 82*, 2051–2060 (2001).
Tratschin et al., *Mol. Cell Biol.*, 5(*11*), 3251–3260 (1985).
Wu, P. et al., *J. Virol.*, 74(*18*), 8635–8647 (2000).
Xiao, W. et al., *J. Virol.*, 73(*5*), 3994–4003 (1999).
Xiao, X. et al., *J. Virol.*, 72(*3*), 2224–2232 (1998).
Yuan et al., *Virology, 279*(*2*), 546–547 (2001).
Xie, Q. et al., *AAV–2, 99*(*16*), 10405–10410 (2002).

pFBD-REP5 cassette pFBDVP-5

PRODUCTION OF ADENO-ASSOCIATED VIRUS IN INSECT CELLS

CROSS-REFERENCE TO RELATED PATENT APPLICATIONS

This patent application is a continuation-in-part of copending U.S. patent application Ser. No. 09/986,618, filed Nov. 9, 2001, which hereby is incorporated by reference.

FIELD OF THE INVENTION

The present invention relates to the production of adeno-associated virus in insect cells.

BACKGROUND OF THE INVENTION

Viruses of the Parvoviridae family are small DNA animal viruses characterized by their ability to infect particular hosts, among other factors. Specifically, the family Parvoviridae is divided between two subfamilies: the Parvovirinae, which infect vertebrates, and the Densovirinae, which infect insects. The subfamily Parvovirinae (members of which herein are referred to as the parvoviruses includes the genus Dependovirus, the members of which are unique in that, under most conditions, these viruses require coinfection with a helper virus such as adenovirus or herpes virus for productive infection in cell culture. The genus Dependovirus includes adeno-associated virus (AAV), which normally infects humans (e.g., serotypes 2, 3A, 3B, 5, and 6) or primates (e.g., serotypes 1 and 4), and related viruses that infect other warm-blooded animals (e.g., bovine, canine, equine, and ovine adeno-associated viruses). The parvoviruses and other members of the Parvoviridae family are generally described in Kenneth I. Berns, "Parvoviridae: The Viruses and Their Replication," Chapter 69 in FIELDS VIROLOGY (3d Ed. 1996).

In recent years, AAV has emerged as a preferred viral vector for gene therapy due to its ability to efficiently infect both nondividing and dividing cells, integrate into a single chromosomal site in the human genome, and pose relatively low pathogenic risk to humans. In view of these advantages, recombinant adeno-associated virus (rAAV) presently is being used in gene therapy clinical trials for hemophilia B, malignant melanoma, cystic fibrosis, and other diseases.

AAV is able to infect a number of mammalian cells. See, e.g., Tratschin et al., *Mol. Cell Biol.,* 5(11):3251–3260 (1985) and Grimm et al., *Hum. Gene Ther.,* 10(15):2445–2450 (1999). However, AAV transduction of human synovial fibroblasts is significantly more efficient than in similar murine cells, Jennings et al., *Arthritis Res,* 3:1 (2001), and the cellular tropicity of AAV differs among serotypes. See, e.g., Davidson et al., *Proc. Natl. Acad. Sci. USA,* 97(7):3428–3432 (2000) (discussing differences among AAV2, AAV4, and AAV5 with respect to mammalian CNS cell tropism and transduction efficiency). Most commonly, rAAV is produced in 293 cells, COS cells, HeLa cells, KB cells, and other mammalian cell lines. See, e.g., U.S. Pat. Nos. 6,156,303, 5,387,484, 5,741,683, 5,691,176, and 5,688,676; U.S. patent application 2002/0081721, and International Patent Applications WO 00/47757, WO 00/24916, and WO 96/17947. Although virus-like particles (VLPs) of parvoviruses have been produced in insect cells (see, e.g., Ruffing et al., *J. Virol.,* 66(12):6922–6930 (1992), Brown et al., *J. Virol.,* 65(5):2702–2706 (1991), and Yuan et al., *Virology,* 279(2):546–547 (2001)), the production of infectious AAV in nonmammalian, invertebrate cells currently is not known. The replication of parvoviral viral genomes, including, particularly, Dependovirus genomes, in nonmammalian, invertebrate cells, is similarly heretofore unknown.

The difficulties involved in scaling-up rAAV production for clinical trials and commercialization using current mammalian cell production systems can be significant, if not entirely prohibitive. For example, for certain clinical studies more than $10^{15}$ particles of rAAV may be required. To produce this number of rAAV particles, transfection and culture with approximately $10^{11}$ cultured human 293 cells, the equivalent of 5,000 175-$cm^2$ flasks of cells, would be required. Related difficulties associated with the production of AAV using known mammalian cell lines are recognized in the art. See, e.g., Grimm et al, supra. There also is the possibility that a vector destined for clinical use produced in a mammalian cell culture will be contaminated with undesirable, perhaps pathogenic, material present in a mammalian cell.

In view of these and other issues there remains a need for alternative and improved methods of efficiently, safely, and economically producing a large amount of infectious rAAV particles. The invention provides such methods. These and other advantages of the invention, as well as additional inventive features, will be apparent from the description of the invention provided herein.

BRIEF SUMMARY OF THE INVENTION

The present invention provides a method of producing AAV in an insect cell. The method comprises providing at least one insect cell-compatible vector. The vector comprises a first nucleotide sequence comprising at least one AAV inverted terminal repeat (ITR) nucleotide sequence, a second nucleotide sequence comprising an open reading frame (ORF) comprising nucleotide sequences encoding AAV VP1, VP2, and VP3 capsid proteins operably linked to at least one expression control sequence for expression in an insect cell, a third nucleotide sequence comprising a Rep52 or a Rep40 coding sequence operably linked to at least one expression control sequence for expression in an insect cell, and a fourth nucleotide sequence comprising a Rep78 or a Rep68 coding sequence operably linked to at least one expression control sequence for expression in an insect cell. The method comprises introducing the at least one vector into an insect cell and maintaining the insect cell under conditions such that AAV is produced.

In accordance with another aspect of the invention, another method of producing AAV in an insect cell is provided. The method comprises providing an insect cell comprising (a) a first nucleotide sequence comprising at least one AAV ITR nucleotide sequence, a second nucleotide sequence comprising an ORF comprising nucleotide sequences encoding AAV VP1, VP2 and VP3 capsid proteins operably linked to at least one expression control sequence for expression in an insect cell, a third nucleotide sequence comprising a Rep52 or a Rep40 coding sequence operably linked to at least one expression control sequence for expression in an insect cell, a fourth nucleotide sequence comprising a Rep78 or a Rep68 coding sequence operably linked to at least one expression control sequence for expression in an insect cell, and, optionally, (b) at least one insect cell-compatible vector. At least one of the first, second, third and fourth nucleotide sequences is/are stably integrated in the insect cell and the at least one insect cell-compatible vector, when present, comprises the remainder of the first, second, third and fourth nucleotide sequences which is/are not stably integrated in the insect cell. The insect cell is maintained under conditions such that AAV is produced.

In accordance with a further aspect of the invention, insect cell-compatible vectors are provided. One vector comprises a nucleotide sequence encoding Rep78 or Rep68 operably linked to a modified early 1 gene (IE-1) promoter from *Orgyia pseudotsugata* (ΔIE-1) and a Kozak-like expression control sequence. Another vector comprises an ORF comprising 3 nucleotide sequences encoding AAV VP1, VP2, and VP3 capsid proteins operably linked to at least one expression control sequence comprising a nine nucleotide sequence of SEQ ID NO:4 or a sequence substantially homologous to SEQ. ID NO: 4, upstream of an initiation codon of the nucleotide sequence encoding AAV VP1 capsid protein, and a C at nucleotide position 2 of the nucleotide sequence encoding AAV VP1 capsid protein.

In yet another aspect of the invention, an insect cell is provided. The insect cell comprises a first nucleotide sequence comprising at least one AAV ITR nucleotide sequence, a second nucleotide sequence comprising an ORF comprising nucleotide sequences encoding AAV VP1, VP2, and VP3 capsid proteins operably linked to at least one expression control sequence for expression in an insect cell, a third nucleotide sequence comprising a Rep52 or a Rep40 coding sequence operably linked to at least one expression control sequence for expression in an insect cell, and a fourth nucleotide sequence comprising a Rep78 or a Rep68 coding sequence operably linked to at least one expression control sequence for expression in an insect cell.

In accordance with another aspect, yet another method of producing AAV in an insect cell is provided. The method comprises providing at least one insect cell-compatible vector comprising a first nucleotide sequence comprising at least one chimeric ITR nucleotide sequence, the ITR nucleotide sequence comprising an AAV backbone and a specific binding and a nicking site of a Rep protein from a parvovirus other than AAV, a second nucleotide sequence comprising an ORF comprising nucleotide sequences encoding AAV VP1, VP2, and VP3 capsid proteins operably linked to at least one expression control sequence for expression in an insect cell, a third nucleotide sequence comprising a Rep52 or a Rep40 coding sequence operably linked to at least one expression control sequence for expression in an insect cell, and a fourth nucleotide sequence comprising a nucleotide sequence encoding a parvoviral Rep protein that can specifically bind and nick the site in the ITR nucleotide sequence within the first nucleotide sequence, operably linked to at least one expression control sequence for expression in an insect cell. The method further comprises introducing the at least one insect cell-compatible vector into an insect cell, and maintaining the insect cell under conditions such that AAV is produced.

The invention also provides a method of producing a parvoviral genome in an insect cell by introducing at least one insect cell-compatible vector into the insect cell and thereafter maintaining the insect cell under conditions such that a parvoviral genome is produced in the cell. The one or more insect cell-compatible vectors used in the method collectively include a first nucleotide sequence comprising at least one parvoviral ITR, a second nucleotide sequence comprising an AAV Rep52 or Rep40 coding sequence operably linked to at least one expression control sequence for expression in an insect cell, and a third nucleotide sequence comprising an AAV Rep78 or Rep68 coding sequence operably linked to at least one expression control sequence for expression in an insect cell.

BRIEF DESCRIPTION OF THE FIGURES

FIG. 5 is a depiction of ITR sequences in palindromic form.

DETAILED DESCRIPTION OF THE INVENTION

The invention described here relates to the remarkable discovery that viruses that normally infect vertebrates can be efficiently produced in insect cells. In a more specific sense, the invention relates to the production of animal parvoviruses, particularly the production of dependoviruses, and, more particularly, the production of infectious human or simian AAV, and the components thereof (e.g., an animal parvovirus genome) in insect cells. All references to AAV and rAAV herein are directed to full "full" virions, i.e., complete particles comprising an AAV genome, rather than, e.g., empty virus capsids or virus-like particles, unless otherwise stated. Such full virions typically are infectious AAV particles able to deliver a transgene into (i.e., transduce) a host cell.

In one embodiment, the invention provides a method of producing an AAV in an insect cell, which method comprises (i) providing at least one insect cell-compatible vector, (ii) introducing the at least one insect cell-compatible vector into an insect cell, and (iii) maintaining the insect cell under conditions such that AAV is produced. The insect-cell vector comprises a first nucleotide sequence comprising at least one AAV ITR nucleotide sequence, a second nucleotide sequence comprising an ORF comprising nucleotide sequences encoding AAV VP1, VP2, and VP3 capsid proteins operably linked to at least one expression control sequence for expression in an insect cell, a third nucleotide sequence comprising a Rep52 or a Rep40 coding nucleotide sequence operably linked to at least one expression control sequence for expression in an insect cell, and a fourth nucleotide sequence comprising a Rep78 or a Rep68 coding nucleotide sequence operably linked to at least one expression control sequence for expression in an insect cell.

Figure 1:
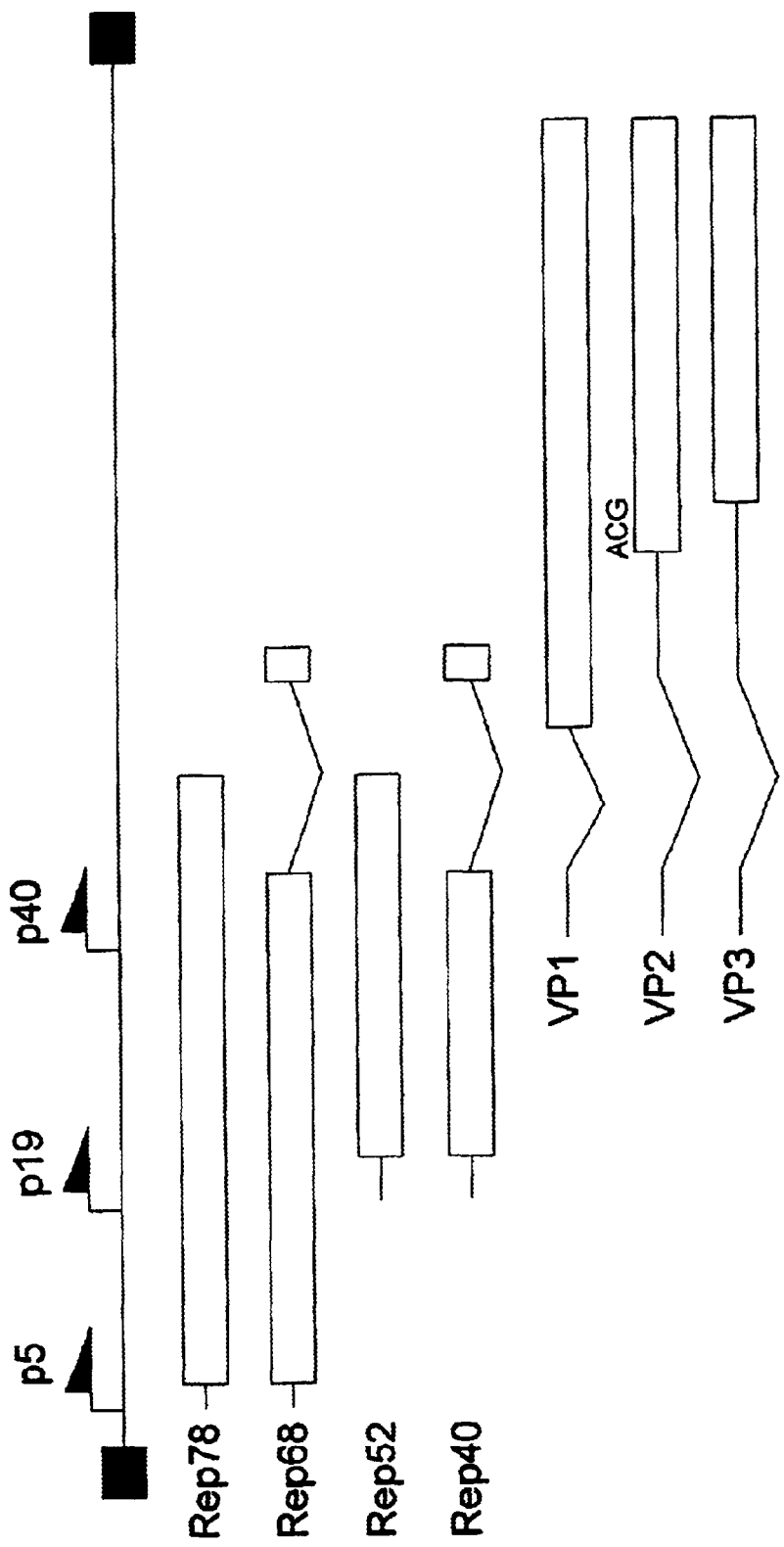
FIG. 1 is a genetic and transcriptional map of an AAV genome.

The genomic organization and transcriptional map shown in FIG. 1 is schematic of all of the known AAV serotypes, serotypes 1–6. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

The AAV sequences employed for the production of AAV in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chiorini et al., *J. Vir.* 71: 6823–33(1997); Srivastava et al., *J. Vir.* 45:555–64 (1983); Chiorini et al., *J. Vir.* 73:1309–1319 (1999); Rutledge et al., *J. Vir.* 72:309–319 (1998); and Wu et al., *J. Vir.* 74: 8635–47 (2000).

AAV Rep and ITR sequences are particularly conserved among most serotypes. For example, the Rep78 proteins of AAV2, AAV3A, AAV3B, AAV4, and AAV6 are reportedly about 89–93% identical. Bantel-Schaal et al., *J. Virol.*, 73(2):939–947 (1999). In fact, it has been reported that AAV2, AAV3A, AAV3B, and AAV6 have 82% total nucleotide sequence identity at the genome level. Id. Moreover, the Rep sequences and ITRs of many AAV serotypes are known to efficiently cross-complement (i.e., functionally substitute) corresponding sequences from other serotypes in production of AAV particles in mammalian cells. The inventors have determined that AAV Rep and ITR sequences also efficiently cross-complement other AAV Rep and ITR sequences in insect cells.

Generally, the VP proteins, which determine the cellular tropicity of the AAV particle, and related VP protein-encoding sequences (which also may be referred to as "cap" sequences), are significantly less conserved than Rep proteins and genes among different AAV serotypes. In view of the ability Rep and ITR sequences to cross-complement corresponding sequences of other serotypes, pseudotyped AAV particles comprising the capsid proteins of a serotype (e.g., AAV3) and the Rep and/or ITR sequences of another AAV serotype (e.g., AAV2) can readily be generated. For example, the inventors have produced high titers of rAAV2/1 and rAAV2/4 (i.e., pseudotyped AAV comprising the ITRs and Rep sequences of AAV2 and VP sequences derived from AAV1 and AAV4, respectively) in Sf9 cells (see Examples 8 and 9, infra). In view of the conserved nature of Rep and ITR sequences among AAV serotypes, production of a pseudotyped vector comprising the VP genes of a particular AAV serotype in a packaging cell system indicates that nonpseudotyped vectors of that serotype also can be successfully produced in that system. For example, the efficient production of rAAV2/1 and rAAV2/4 in Sf9 cells indicates that rAAV1 and rAAV4 also can be efficiently produced in these cells.

In view of the foregoing, it will be understood that sequences from more than one AAV serotype can be combined for production of AAV in insect cells. For example, the first nucleotide sequence comprising at least one AAV ITR nucleotide sequence can be derived from one serotype, for example AAV2, while any of the other first, second, third, and fourth nucleotide sequences can comprise open reading frames or coding sequences derived from one or more other serotypes, for example, serotype 3. AAV serotypes 1, 2, 3, 4 and 5 are preferred source of AAV nucleotide sequences for use in the context of the present invention.

In a preferred and related aspect, the above-described first nucleotide sequence of the inventive method comprises an AAV1, AAV2, or AAV4 ITR, the above-described third nucleotide sequence comprises an AAV1, AAV2, or AAV4 Rep52 or Rep40 coding sequence, and the above-described fourth nucleotide sequence comprises an AAV1, AAV2, or AAV4 Rep78 or Rep68 coding sequence. In a more particular aspect, the above-described second nucleic acid encodes VP1, VP2, and VP3 proteins of AAV1, AAV2, or AAV4.

Modified "AAV" sequences also can be used to produce rAAV vectors in insect cells. For example, or more sequences having at least about 70%, at least about 75%, at least about 80%, at least about 85%, at least about 90%, at least about 95%, or more nucleotide and/or amino acid sequence identity (e.g., a sequence having about 75–99% nucleotide sequence identity) to an AAV1, AAV2, AAV3, and/or AAV4 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. For example, AAV5 Rep and ITR sequences are unable to efficiently cross-complement corresponding Rep and ITR sequences from AAV2 in mammalian cells. See, e.g., Chiorini et al., *J. Virol.*, 73(5):4293–4298 (1999) and Chiorini et al., *J. Virol.*, 73(2):1309–1319 (1999). This lack of functional homology in AAV5 Rep and ITR sequences may be due to the relatively significant differences in the nucleotide and amino acid sequences of AAV5 from the corresponding sequences of other AAV serotypes. See, e.g., Bantel-Schaal et al., *J. Virol.*, 73(2):939–947 (1999). In view of these differences, the production of AAV5 can differ from production of other serotypes. For example, the use of AAV5 Rep and ITR sequences can be less suitable than sequences from serotypes 1, 2, 3, and 4 in the context of producing pseudotyped AAV vectors. Despite these and other differences between AAV5 and other human and simian serotypes, the inventors have discovered that rAAV5 and rAAV vectors comprising AAV5 capsid proteins can be produced in insect cells in accordance with the present invention. Where methods of the invention are employed produce rAAV5, it is preferred that one or more vectors comprising, collectively in the case of more than one vector, a nucleotide sequence comprising an AAV5 ITR, a nucleotide sequence comprises an AAV5 Rep52 and/or Rep40 coding sequence, and a nucleotide sequence comprises an AAV5 Rep78 and/or Rep68 coding sequence. Such ITR and Rep sequences can be modified as desired to obtain efficient production of rAAV5 or pseudotyped rAAV5 vectors in insect cells (e.g., the start codon of the Rep sequences can be modified, VP splice sites can be modified or eliminated, and/or the VP1 start codon and nearby nucleotides can be modified to improve the production of rAAV5 in the insect cell). Modifying AAV Rep and/or VP sequences to produce modified Rep and/or VP sequences, which modified Rep and/or VP sequences facilitate AAV and AAV genome production in insect cells (e.g., the production of at least about 1 AAV vector genome/cell), whether in AAV5 and other AAV serotypes, through such start codon substitutions, codon context modifications, particularly by modifying the nucleotide sequences near the VP1 start codon, and other nucleotide sequence modifications described herein (e.g., the elimination of VP sequence splice sites, false codons, and selection of appropriate promoters) is another important feature of the invention.

A full complement of VP capsid proteins comprises VP1, VP2, and VP3. The ORF comprising nucleotide sequences encoding AAV VP capsid proteins may comprise less than a full complement of VP proteins. However, in a preferred embodiment, the full complement of VP proteins is provided. It is possible to produce the VP proteins from a nucleotide sequence encoding less than VP1, VP2, and VP3 by use, for example, of separate nucleotide sequences operably linked to at least one expression control sequence for expression in an insect cell, each producing only one VP capsid protein. In a preferred embodiment, the second nucleotide sequence comprises one ORF comprising nucleotide sequences encoding VP1, VP2, and VP3 capsid proteins operably linked to at least one expression control sequence for expression in an insect cell.

Any insect cell which allows for replication of AAV and which can be maintained in culture can be used in accordance with the present invention. For example, the cell line used can be from *Spodoptera frugiperda,* such as the Sf9 or Sf21 cell lines, drosophila cell lines, or mosquito cell lines, e.g., *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, NJ (1995); O'Reilly et al., BACULOVIRUS EXPRESSION VECTORS, A LABORATORY MANUAL, Oxford Univ. Press (1994); Samulski et al., *J. Vir.* 63:3822–8 (1989); Kajigaya et al., *Proc. Nat'l. Acad. Sci. USA* 88: 4646–50 (1991); Ruffing et al., *J. Vir.* 66:6922–30 (1992); Kimbauer et al., *Vir.* 219:37–44 (1996); Zhao et al., *Vir.* 272:382–93 (2000); and Samulski et al., U.S. Pat. No. 6,204,059. A preferred cell line is the *Spodoptera frugiperda* Sf9 cell line.

By "insect cell-compatible vector" or "vector" is meant any compound or formulation, biological or chemical, which formulation facilitates transformation or transfection of an insect with a nucleic acid. Exemplary biological vectors include plasmids, linear nucleic acid molecules, and recombinant viruses. Exemplary chemical vectors include lipid complexes. Biologically functional vectors capable of expression and replication in an insect cell are known in the art. Such vectors are used to incorporate nucleic acid sequences into insect cells in accordance with the present invention. O'Reilly et al. (1994), supra; MOLECULAR CLONING, Maniatis et al., eds. CSH Laboratory, NY, N.Y. (1982); and LIPOSOMES AS TOOLS IN BASIC RESEARCH AND INDUSTRY, Philiport and Scluber, eds. CRC Press, Ann Arbor, Mich. (1995).

The invention is not limited by the vector used to introduce the AAV functions into the insect cell. Any vector can be employed as long as it is insect cell-compatible. The presence of the vector in the insect cell need not be permanent. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus.

The number of vectors employed is not limiting of the invention. For example, one, two, three, four, five, six, or more vectors can be employed to produce AAV in insect cells in accordance with the present inventive method. If six vectors are employed, one vector encodes AAV VP1, another vector encodes AAV VP2, yet another vector encodes AAV VP3, still yet another vector encodes Rep52 or Rep40, while Rep78 or Rep 68 is encoded by another vector and a final vector comprises at least one AAV ITR. Additional vectors might be employed to express, for example, Rep52 and Rep40, and Rep78 and Rep 68. If fewer than six vectors are used, the vectors can comprise various combinations of the at least one AAV ITR and the VP1, VP2, VP3, Rep52/Rep40, and Rep78/Rep68 coding sequences. Preferably, two vectors or three vectors are used, with two vectors being more preferred.

Figure 3:
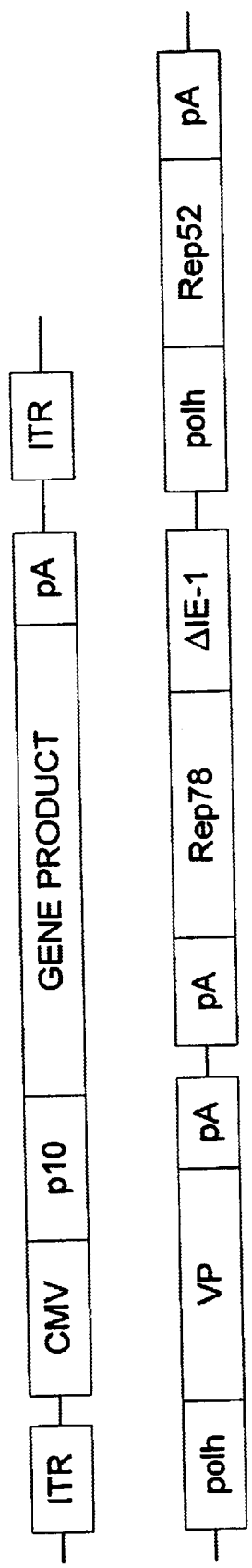
FIG. 3 is a genetic map of an exemplary two-vector system for production of rAAV in insect cells.

If two vectors are used, preferably the first vector comprises the first nucleotide sequence comprising at least one AAV ITR nucleotide sequence, and the second vector comprises the second nucleotide sequence comprising an ORF comprising nucleotide sequences encoding AAV VP1, VP2 and VP3 capsid proteins operably linked to at least one expression control sequence for expression in an insect cell, the third nucleotide sequence comprising a Rep52 or a Rep40 coding sequence operably linked to at least one expression control sequence for expression in an insect cell, and the fourth nucleotide sequence comprising a Rep78 or a Rep68 coding sequence operably linked to at least one expression control sequence for expression in an insect cell. FIG. 3 is a genetic map of an exemplary two-vector system. In FIG. 3, pA is a polyadenylation signal, polh and ΔIE-1 are transcriptional promoters for expression in insect cells, and CMV and p10 are respectively, mammalian transcriptional and insect specific promoters for expression of a desired gene in a mammalian or insect cell.

Figure 4:
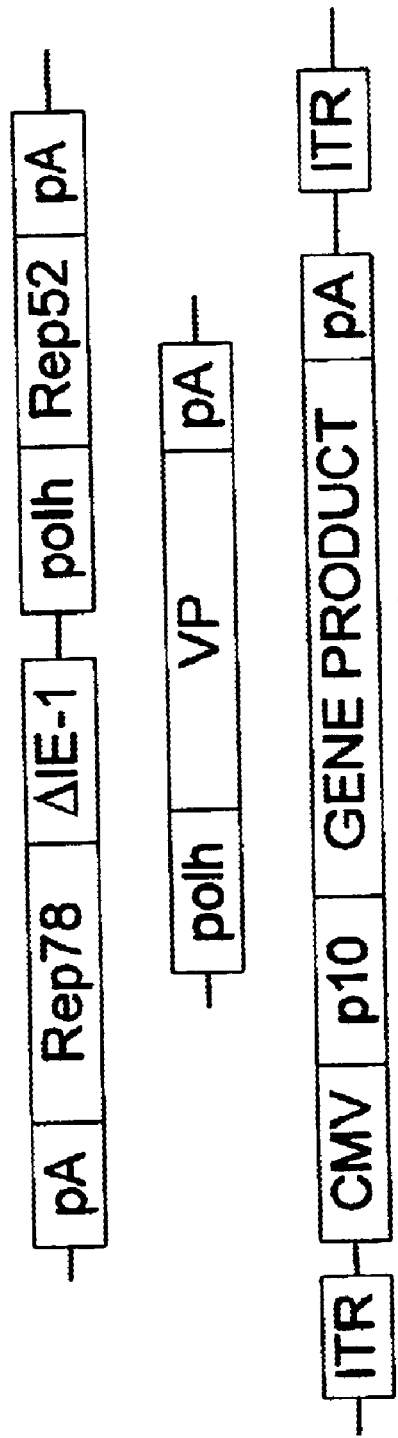
FIG. 4 is a genetic map of an illustrative three-vector system for production of rAAV in insect cells.

If three vectors are used, preferably the first vector comprises the first nucleotide sequence comprising at least one AAV ITR nucleotide sequence, the second vector comprises the second nucleotide sequence comprising an ORF comprising nucleotide sequences encoding AAV, VP1, VP2 and VP3 capsid proteins operably linked to at least one expression control sequence for expression in an insect cell, and the third vector comprises the third nucleotide sequence comprising a Rep52 or a Rep40 coding sequence operably linked to at least one expression control sequence for expression in an insect cell, and the fourth nucleotide sequence comprising a Rep78 or a Rep68 coding sequence operably linked to at least one expression control sequence for expression in an insect cell. FIG. 4 is a genetic map of an exemplary three-vector system. In FIG. 4, pA is a polyadenylation signal, polh and ΔIE-1 are transcriptional promoters for expression in insect cells, and CMV and p10 are respectively, mammalian transcriptional and insect specific promoters for expression of a desired gene in a mammalian or insect cell.

The sequences on each vector can be in any order relative to each other. For example, if one vector comprises ITRs and an ORF comprising nucleotide sequences encoding VP capsid proteins, the VP ORF can be located on the vector such that, upon replication of the DNA between ITR sequences, the VP ORF is replicated or not replicated. For another example, the Rep coding sequences and/or the ORF comprising nucleotide sequences encoding VP capsid proteins can be in any order on a vector.

In accordance with one embodiment of the invention, a method of producing an AAV in an insect cell is provided, comprising providing an insect cell comprising a first nucleotide sequence comprising at least one AAV ITR nucleotide sequence, a second nucleotide sequence comprising an ORF comprising nucleotide sequences encoding AAV VP1, VP2 and VP3 capsid proteins operably linked to at least one expression control sequence for expression in an insect cell, a third nucleotide sequence comprising a Rep52 or a Rep40 coding sequence operably linked to at least one expression control sequence for expression in an insect cell, and a fourth nucleotide sequence comprising a Rep78 or a Rep68 coding sequence operably linked to at least one expression control sequence for expression in an insect cell.

Optionally, at least one insect cell-compatible vector is provided. At least one of the first, second, third and fourth nucleotide sequences is/are stably integrated in the insect cell and, the at least one insect cell-compatible vector, when present, comprises the remainder of the first, second, third and fourth nucleotide sequences which is/are not stably integrated in the insect cell. The insect cell, comprising the first to fourth nucleotide sequences and, optionally, the at least one insect cell-compatible vector, is maintained under conditions such that AAV is produced. Preferably, the second nucleotide sequence is stably integrated in the insect cell.

As discussed above, growing conditions for insect cells in culture, and production of heterologous products in insect cells in culture are well-known in the art. See Richard (1995), supra; O'Reilly et al., (1994) supra; Samulski et al., (1989) supra; Kajigaya et al., (1991) supra; Ruffing et al., (1992) supra; Kirnbauer et al., (1996) supra; Zhao et al., (2000) supra; and Samulski et al., U.S. Pat. No. 6,204,059.

One of ordinary skill in the art knows how to introduce stably a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome. Often, a cell which underwent such "transformation," i.e., addition of a nucleic acid sequence to the cell, is selected or identified by expression of a marker gene which, usually, is encoded by the nucleic acid sequence added to the cell. The incorporation of the nucleic acid sequence in the genome then can be determined by, for example, Southern blots or polymerase chain reaction (PCR) methods.

Figure 5A:
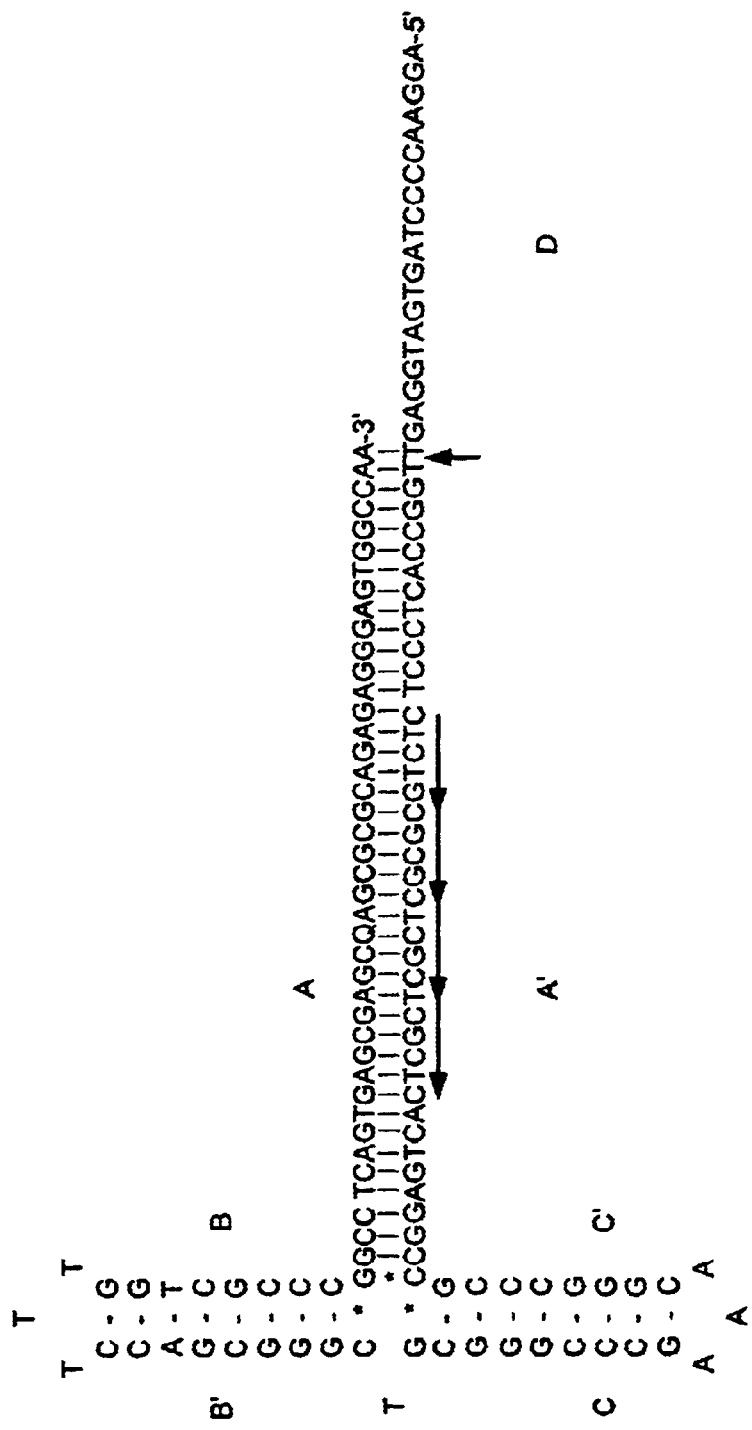
FIG. 5A shows the AAV2 ITR sequence.

By "at least one AAV ITR nucleotide sequence" is meant a palindromic sequence, comprising mostly complementary, symmetrically arranged sequences also referred to as "A," "B," and "C" regions. The ITR functions as an origin of replication, a site having a "cis" role in replication, i.e., being a recognition site for trans acting replication proteins (e.g., Rep 78 or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. FIG. 5A shows an AAV2 palindrome and indicates the A, B, C, and D regions. An AAV replicating in a mammalian cell typically has two ITR sequences.

It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for AAV replication of a circular vector. Thus, one ITR nucleotide sequence can be used in the context of the present invention. Preferably, however, two or another even number of regular ITRs are used. Most preferably, two ITR sequences are used.

Each of Rep78 and Rep68 is part of a replication mechanism in which it binds to unique and known sequence on the ITR (also known as a binding site) comprising short and repeated nucleotide sequences located on the A region of the ITR, and nick the DNA at a known site, typically 5' of a thymidine nucleotide located 5' of the binding site at the beginning of the D region (the nick site). In addition to specific binding to sequences of ITR and nicking, Rep78 or Rep68 exerts an ATP-dependent helicase activity for unwinding double-stranded DNA. In these respects, Rep78 and Rep68 are typical of Rep proteins from parvoviruses.

One concern in viral vector construction is the safety of such viral vectors. An issue which arises in clinical use of a viral vector is the sometimes undesirable ability of the vector to further propagate after initial introduction into a cell. The invention provides a safety mechanism for limiting undesirable vector propagation in a recipient.

In accordance with this aspect of the invention, the safety of viral vectors is improved by using a vector for rAAV production comprising nucleotide sequences providing the rAAV with a chimeric ITR, thereby providing a means to interfere with the ability of the rAAV to replicate in the presence of a second AAV virus. An rAAV genome comprising such a chimeric ITR then can only be replicated by the Rep or Rep protein equivalent which is capable of binding the chimeric ITR. A chimeric ITR will have a binding site for a Rep protein or Rep protein equivalent and a nicking site. One example of such a chimeric ITR, which is particularly useful in baculovirus systems for producing rAAV, employs a binding site which is specific for the insect Rep protein, NS-1.

Figure 5B:
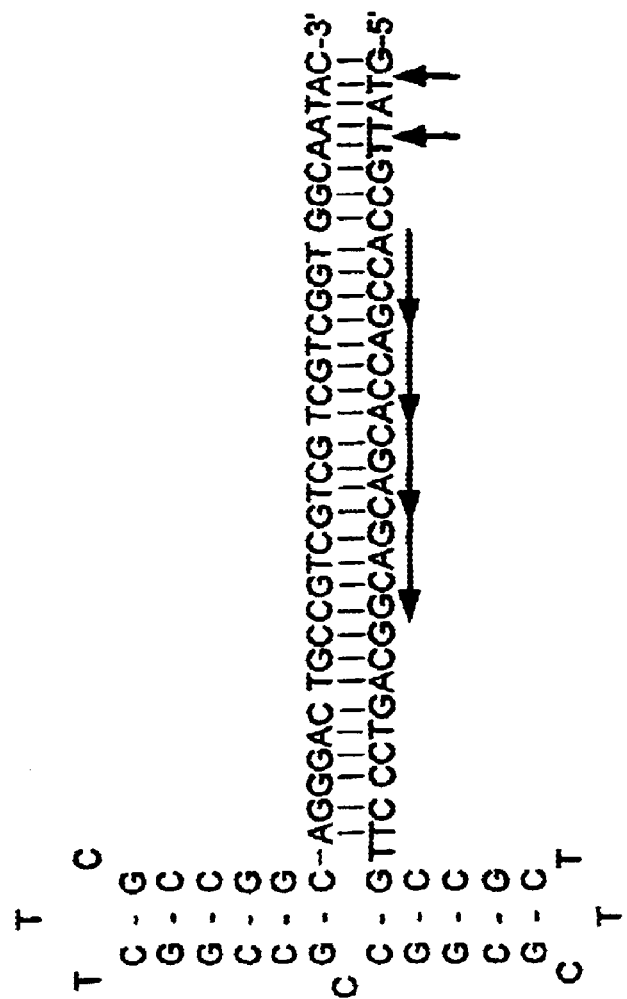
FIG. 5B shows the JcDNV ITR sequence.
Figure 5C:
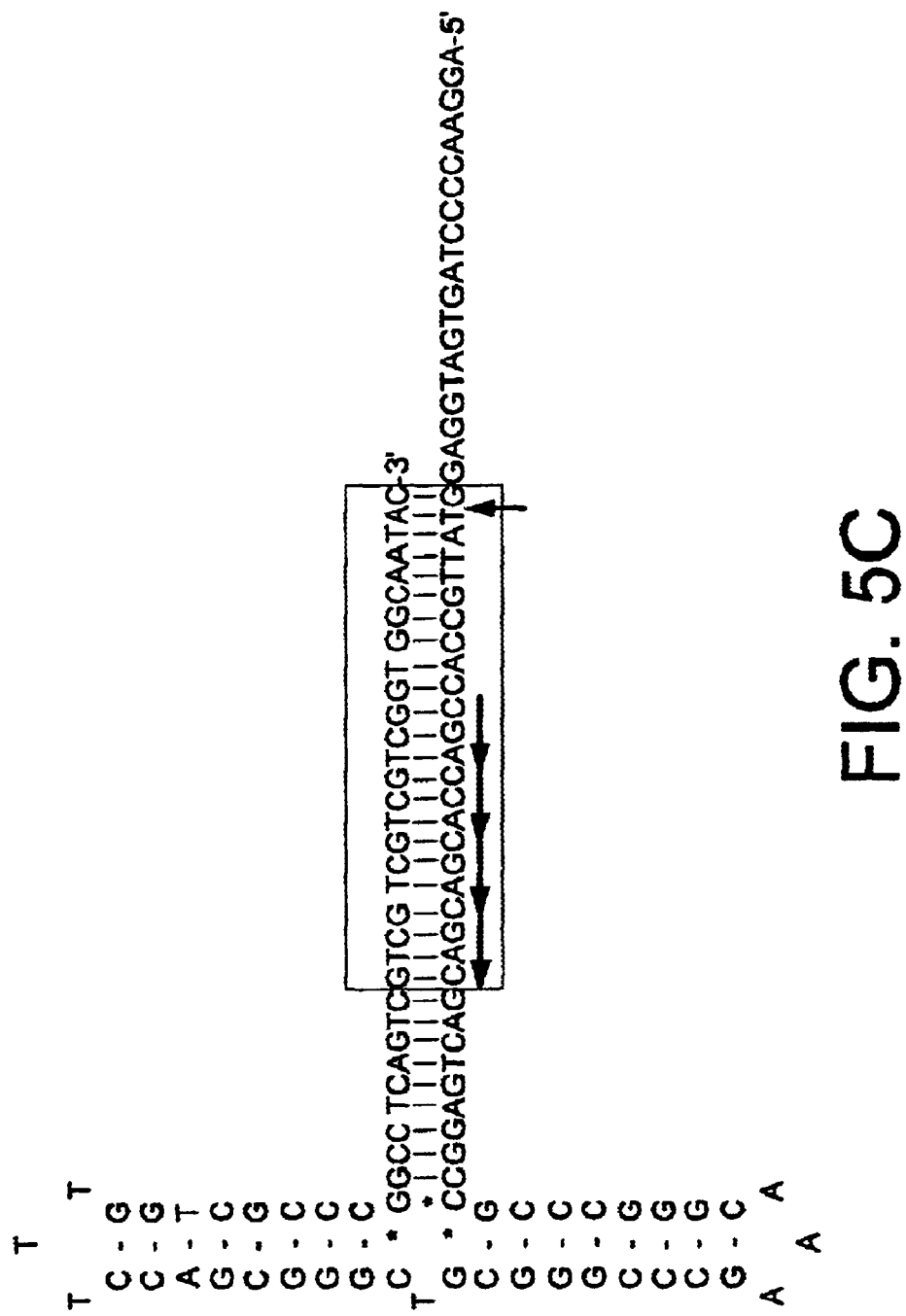
FIG. 5C shows a representative chimeric AAV2/JcDNV ITR sequence.

An example of a Rep protein equivalent from a parvovirus other than AAV is the non-structural protein NS-1 from *Junonia coenia* densovirus (JcDNV). Although the JcDNV genome and the NS-1 gene sequence were known (see, e.g., Dumas et al., *Virology* 191:202–122 (1992) and Tijssen, et al., *Semin. Virol.* 6:347–55 (1995)), the ability of the NS-1 protein to function in a manner equivalent to that of the Rep protein of AAV was not known. As described herein, the inventors have demonstrated that NS-1 has binding/nicking and ATP-dependent helicase activities closely matching the Rep of other parvoviruses. See also, Ding et al., *J. Virol.,* 76(1):338–345 (2002). In particular, these activities are similar to those of AAV Rep78 and Rep68. The binding site for NS-1 is four repeats of a GAC sequence, and the nick site is G*TATTG, where "*" indicated an internucleotide bond that is likely nicked in vivo. FIG. 5B shows the JcDNV ITR and indicates the binding and nicking sites. FIG. 5C shows a chimeric ITR, specifically a AAV2/JcDNV ITR, where the ITR backbone was altered to include NS-1 binding and nick sites.

Although the chimeric vector exemplified above utilizes the binding site and nick sequence for the JcDNV Rep protein, the chimeric ITRs of this application should not be limited thereto. Parvoviruses other than AAV, (e.g., vertebrate parvoviruses and insect parvoviruses, referred to as densoviruses), like AAV, have one or more Rep proteins or the equivalents thereof, which specifically bind their ITRs or nick single-stranded DNA, and display ATP-dependent helicase activities. Knowledge of the specific binding site within the ITR or equivalent and nick sequences for other parvoviruses allows construction of chimeric ITRs for vectors having an AAV backbone. Therefore, one of ordinary skill in the art recognizes that other chimeric ITRs can be engineered using other parvoviruses.

In accordance with an embodiment of the invention, the first nucleotide sequence comprises at least one chimeric ITR nucleotide sequence comprising an AAV backbone and a specific binding and nicking site of a Rep protein from a parvovirus other than AAV and the fourth nucleotide sequence comprises a nucleotide sequence encoding a parvoviral Rep protein that can specifically bind and nick the site in the ITR nucleotide sequence within the first nucleotide sequence. In a more preferred embodiment, the chimeric ITR is the AAV2/JcDNV ITR sequence represented in FIG. 5C and the nucleotide sequence encoding Rep coding sequence is that of NS-1.

The first nucleotide sequence can further comprise a nucleic acid sequence encoding at least one "gene product of interest" for expression in a mammalian cell, located such that it will be incorporated into an AAV genome replicated in the insect cell. Any nucleic acid can be incorporated for later expression in a mammalian cell transfected with the AAV produced in accordance with the present invention. For example, the nucleic acid can encode a protein or express antisense RNA. The protein can be a secretable protein, or a protein which will affect primarily the cell that is infected with the insect-produced AAV. In accordance to a preferred embodiment, one product of interest is Rep78 or Rep68. In accordance with a preferred embodiment, the first nucleotide sequence comprises two nucleic acid sequences and each encodes one gene product of interest for expression in a mammalian cell. Each of the two nucleic acid sequences encoding a product of interest is located such that it will be incorporated into a rAAV genome replicated in the insect cell.

Generally, a product of interest is a gene product which can be a polypeptide, RNA molecule, or other gene product that is desired for expression in the mammalian cell. A product of interest can include, for example, polypeptides that serve as marker proteins to assess cell transformation and expression, fusion proteins, polypeptides having a desired biological activity, gene products that can complement a genetic defect, RNA molecules, transcription factors, and other gene products that are of interest in regulation and/or expression. For example, gene products of interest include nucleotide sequences that provide a desired effect or regulatory function (e.g., transposons, transcription factors). Examples of gene products of interest include, but are not limited to: hormone receptors (e.g., mineralcorticosteroid, glucocorticoid, and thyroid hormone receptors); intramembrane proteins (e.g., TM-1 and TM-7); intracellular receptors (e.g., orphans, retinoids, vitamin D3 and vitamin A receptors); signaling molecules (e.g., kinases, transcription factors, or molecules such signal transducers and activators of transcription receptors of the cytokine superfamily (e.g. erythropoietin, growth hormone, interferons, and interleukins, and colony-stimulating factors; G-protein coupled receptors, e.g., hormones, calcitonin, epinephrine, gastrin, and paracrine or autocrine mediators, such as stomatostatin or prostaglandins; neurotransmitter receptors (norepinephrine, dopamine, serotonin or acetylcholine); pathogenic antigens, which can be of viral, bacterial, allergenic, or cancerous origin; and tyrosine kinase receptors (such as insulin growth factor, and nerve growth factor). Gene products currently used in AAV-mediated gene therapy trials also are important gene products (e.g., CFTR and Factor IX).

A gene product of interest can be a therapeutic gene product. A therapeutic gene product is a polypeptide, RNA molecule, or other gene product that, when expressed in a target cell, provides a desired therapeutic effect, e.g., ablation of an infected cell, expression of a polypeptide having a desired biological activity, and/or expression of an RNA molecule for antisense therapy (e.g., regulation of expression of a endogenous or heterologous gene in the target cell genome). For example, Goldsmith et al., WO 90/07936, described a system for ablating specific cells within a tissue by using a promoter that is activated only in that tissue to express a therapeutic gene product only in the desired cells. For example, in a patient about to receive a heterologous transplant or graft, one may administer a polynucleotide encoding a toxin to T cells targeting the graft.

An AAV protein can be a gene product of interest. For example, the sequence of a Rep protein, such as Rep78 or Rep68, or a functional fragment thereof can be a gene product of interest for expression in the mammalian cell. A nucleic acid sequence encoding Rep78 and/or Rep68, if present on the rAAV genome of the invention and expressed in a mammalian cell transduced with the rAAV produced in accordance with the present invention, allows for integration of the rAAV into the genome of the transduced mammalian cell. Expression of Rep78 and/or Rep68 in an rAAV-transduced or infected mammalian cell can bestow an advantage for certain uses of the rAAV produced in an insect cell, by allowing long term or permanent expression of any other gene product of interest introduced in the cell by the rAAV.

A selectable marker is one type of a gene product of interest. A selectable marker is a gene sequence or a protein encoded by that gene sequence. Expression of the protein encoded by the selectable marker allows a host cell transfected with an expression vector which includes the selectable marker to be easily identified from a host cell which does not have an expression vector encoding the selectable marker. An example is a host cell which can use the selectable marker to survive a selection process that would otherwise kill the host cell, such as treatment with an antibiotic. Such a selectable marker can be one or more antibiotic resistance factors, such as neomycin resistance (e.g., neo), hygromycin resistance, and puromycin resistance. A selectable marker also can be a cell-surface marker, such as nerve growth factor receptor or truncated versions thereof. Cells that express the cell-surface marker then can be selected using an antibody targeted to the cell-surface marker. The antibody targeted to the cell surface marker can be directly labeled (e.g., with a fluorescent substrate) or can be detected using a secondary labeled antibody or substrate which binds to the antibody targeted to the cell-surface marker. Alternatively, cells can be negatively selected by using an enzyme, such as Herpes simplex virus thymidine kinase (HSVTK) that converts a pro-toxin (gancyclovir) into a toxin or bacterial Cytosine Deaminase (CD) which converts the pro-toxin 5'-fluorocytosine (5'-FC) into the toxin 5'-fluorouracil (5'-FU). Alternatively, any nucleic acid sequence encoding a polypeptide can be used as a selectable marker as long as the polypeptide is easily recognized by an antibody.

The nucleic acid encoding a selectable marker can encode, for example, a β-lactamase, a luciferase, a green fluorescent protein (GFP), β-galactosidase, or other reporter gene as that term is understood in the art, including cell-surface markers, such as CD4 or the truncated nerve growth factor (NGFR) (for GFP, see WO 96/23810; Heim et al., *Current Biology* 2:178–182 (1996); Heim et al., *Proc. Natl. Acad. Sci. USA* (1995); or Heim et al., *Science* 373:663–664 (1995); for β-lactamase, see WO 96/30540). In a preferred embodiment, the selectable marker is a β-lactamase. The nucleic acid encoding a selectable marker can encode, for example, a fluorescent protein. A fluorescent protein can be detected by determining the amount of any quantitative fluorescent property, e.g., the amount of fluorescence at a particular wavelength, or the integral of fluorescence over an emission spectrum. Optimally, the fluorescent protein is selected to have fluorescent properties that are easily detected. Techniques for measuring fluorescence are well-known to one of skill in the art.

In accordance with the invention, the nucleic acid for expression in the mammalian cell will be incorporated into the AAV genome produced in the insect cell if it is located between two regular ITRs, or is located on either side of an ITR engineered with two D regions.

In the at least one nucleotide sequence encoding a gene product of interest for expression in a mammalian cell, the nucleotide sequence(s) is/are operably linked to at least one mammalian cell-compatible expression control sequence, e.g., a promoter. Many such promoters are known in the art. It will be understood by a skilled artisan that preferred promoters include those that are inducible, tissue-specific, or cell cycle-specific. For example, it was reported that the E2F promoter can mediate tumor-selective, and, in particular, neurological cell tumor-selective expression in vivo by being de-repressed in such cells in vivo. Parr et al., *Nat. Med.* 3:1145–9 (1997).

The VP and Rep coding nucleotide sequences (i.e., those comprised within second, third, and fourth nucleotide sequences) are operably linked to at least one expression control sequence for expression in an insect cell. Herein, "coding nucleotide sequences" refer to that portion of a nucleotide sequence that is translated into a protein product. "Operably linked" means that the expression control sequence is positioned relative to the coding sequence such that it can promote the expression of the encoded gene product.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

More than one expression control sequence can be operably linked to a given nucleotide sequence. For example, a promoter sequence, a translation initiation sequence, and a stop codon can be operably linked to a nucleotide sequence.

The translational start site of eukaryotic mRNA is controlled in part by a nucleotide sequence referred to as a Kozak sequence. See Kozak, *Cell* 44:283–292 (1986); Kozak, J., *Cell. Biol.* 108: 229–41 (1989). Both naturally occurring and synthetic translational start sites of the Kozak form can be used in the production of polypeptides by molecular genetic techniques. Kozak, *Mamm. Genome* 7:563–574 (1996).

Splice sites are sequences on a mRNA which facilitate the removal of parts of the mRNA sequences after the transcription (formation) of the mRNA. Typically, the splicing occurs in the nucleus, prior to mRNA transport into a cell's cytoplasm.

An expression control sequence can be homologous to known expression control sequences. A determination of the degree of homology of two nucleic acids sequences is a determination of the percentage of time a nucleotide, from among the four known natural nucleotides, exactly matches a counterpart on a second nucleotide sequence, e.g. a T matches a T, an A matches an A, a G matches a G, and a C matches a C. A homology of at least 50%, 60%, 70%, preferably 80%, more preferably 90% or more, is considered to be a substantially homologous expression control sequence. Preferably, the homology is calculated between sequences without introduction of gaps in one or both of the sequences being compared.

A skilled artisan will understand that in order to optimize the homology between two nucleotide sequences, gaps can be introduced in either or both of the two sequences. Preferably, if gaps are introduced, only nucleotides which pair with a nucleotide in the second nucleotide sequence (whether or not there is a match) are used to calculate percentage homology. Algorithms that have worked out the rules of calculation of percentage homology are known. Examples of such programs include the SIM, GAP, NAP, LAP2, GAP2, ALIGN, BLAST, and PIPMAKER.

For example, the ALIGN program produces an optimal alignment of two chosen protein or nucleic acid sequences using a modification of the dynamic programming algorithm described by Myers and Miller, CABIOS, 4, 11–17 (1988). Preferably, if available, the ALIGN program is used with weighted end-gaps. If gap opening and gap extension penalties are available, they are preferably set between about −5 to −15 and 0 to −3, respectively, more preferably about −12 and −0.5 to −2, respectively, for amino acid sequence alignments, and −10 to −20 and −3 to −5, respectively, more preferably about −16 and −4, respectively, for nucleic acid sequence alignments. The ALIGN program and principles underlying it are further described in, e.g., Pearson et al., *Proc. Natl. Acad. Sci. USA,* 85: 2444–48 (1988), and Pearson et al., *Methods Enzymol.* 183:63–98 (1990).

The BLAST programs provide analysis of at least two amino acid or nucleotide sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations (see, e.g., Wooton et al., *Compu. Chem.,* 17:149–63 (1993); Altschul et al., *Nat. Genet.,* 6: 119–29 (1994); Hancock et al., *Comput. Appl. Biosci.,* 10:67–70 (1994); and Wootton et al., *Meth. in Enzym.,* 266:554–71 (1996)). If a lambda ratio is used, preferred settings for the ratio are between 0.75 and 0.95, more preferably between 0.8 and 0.9. If gap existence costs (or gap scores) are used, the gap existence cost preferably is set between about −5 and −15, more preferably about −10, and the per residue gap cost preferably is set between about 0 to −5, more preferably between 0 and −3 (e.g., −0.5). Similar gap parameters can be used with other programs as appropriate. The BLAST programs and principles underlying them are further described in, e.g., Altschul et al., *J. Mol. Biol.,* 215: 403–10 (1990), Karlin and Altschul, *Proc. Natl. Acad. Sci. USA,* 87: 2264–68 (1990) (as modified by Karlin and Altschul, *Proc. Natl. Acad. Sci. USA,* 90: 5873–77 (1993)), and Altschul et al., *Nucl. Acids Res.,* 25: 3389–3402 (1997).

The method of the invention is not limited by the use of specific expression control sequences. However, when a certain stoichiometry of VP products are achieved (close to 1:1:10 for VP1, VP2, and VP3, respectively) and also when the levels of Rep52 or Rep40 (also referred to as the p19 Reps) are significantly higher than Rep78 or Rep68 (also referred to as the p5 Reps), the best yields of AAV in insect cell are obtained. Preferably, the p5/p19 ratio is below 0.6, more preferably below 0.4, more preferably yet, below 0.3, but always at least 0.03. These ratios can be measured at the level of the protein or can be implicated from the relative levels of specific mRNAs.

Figure 2:
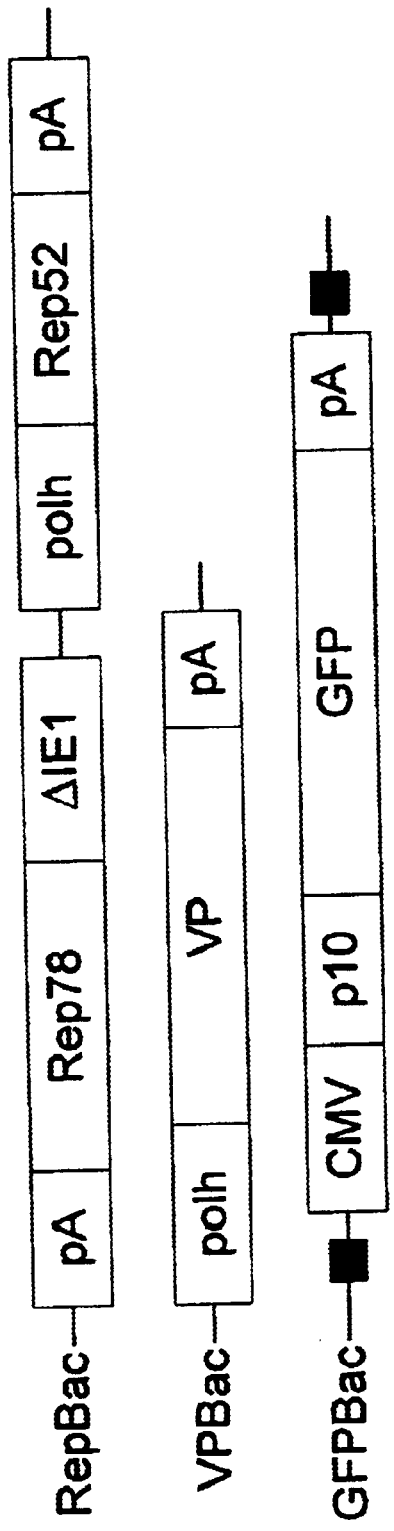
FIG. 2 is a genetic map of representative recombinant baculoviruses employed to produce rAAV in insect cells.

Below are examples of considerations for the expression and examples of expression control sequences employed in various preferred embodiments of the invention. FIG. 2 presents a genetic map showing promoters and location of pA sequences used in some preferred embodiments of the invention.

In AAV produced in mammalian cells, the four Rep proteins are derived from a single ORF. Promoters at map positions 5 and 19 regulate transcription of the Rep ORF. Rep78 and 68 are expressed from the p5 promoter and differ from each other by a 3'-splice. Rep68 is essentially a carboxy-truncated version of Rep78, although Rep68 contains 7 unique residues as a result of a frame shift occurring in the splice acceptor site. The Rep52 and Rep40 transcripts are expressed by the p19 promoter and are in-frame with the larger Rep proteins. The smaller Rep proteins differ from each other in the same manner as Rep78 and Rep68, i.e., by a splicing event. The functional domains of Rep are: Amino terminus—DNA binding—DNA nicking—ATPase—Helicase—nuclear localization signal—modified zinc finger—COOH. The functions in bold are present only in the p5 Rep proteins. AAV replicates via a duplex DNA intermediate that is one continuous molecule: both strands are covalently attached through the ITR. The p5 Rep proteins are able to recognize a motif within the ITR and nick one strand of the duplex becoming covalently attached through the tyrosinyl-thymidine phosphodiester linkage at the 5'-side of the nick. The helicase activity of Rep is apparently responsible for unwinding the newly created 5'-end and a cellular polymerase complex extending the recessed 3'-end to generate a duplex, blunt-ended replication intermediate. The smaller Rep proteins retain the ATP-dependent, DNA helicase activity and are involved in encapsidation of the single-stranded virion genomes. Rep52 and Rep40 associate with the preformed capsids and, presumably, unwind the duplex replication intermediates.

In practicing the methods of the invention, it is possible to use less than the four Rep enzymes, such as only one of the Rep78/Rep68 enzymes and only one of the Rep52/Rep40 enzymes, wherein each of the two Rep enzymes is separately expressed. It is noted that in mammalian cells the mRNAs corresponding to Rep68 and Rep40 require splicing (removal of an intron sequence) to result in a mRNA which can be translated into a functional Rep68 or Rep40. It was determined that Rep mRNA splicing in insect cells does not mimic the process in mammalian cells. Thus, a Rep68 or Rep40 coding nucleotide sequence was engineered to be devoid of the intron, i.e., a contiguous nucleic acid sequence which will be translated comprises the engineered coding sequence. Now, the coding sequence within any mRNA transcribed will not require the splicing out (removal) of part of the mRNA before translation. Such engineering is well within the knowledge of an ordinarily skilled artisan as the Rep gene sequence is known and techniques to engineer the gene without the intron comprise standard molecular biology techniques. Preferably, the Rep sequences expressed in the insect cell are Rep78 and Rep52.

As discussed above, any transcriptional promoters compatible with insect cell gene expression can be employed. However, the stoichiometry of Rep78 or Rep68 to Rep52 or Rep40 protein is important for optimum AAV production. Less Rep78 or Rep68 than Rep52 or Rep40 is desired.

In accordance with one embodiment of the invention, Rep52 or Rep40 is transcribed from the baculovirus derived polyhedron promoter, (polh). Rep78 or Rep68 is transcribed from a weaker promoter, for example the IE-1 promoter, which can be derived from pIZT/V5-His vector sold by Invitrogen (nucleotides 2345–2636 of the vector). See also Theilmann and Stewart, *Vir.* 180:492–508 (1991). Preferably, a promoter substantially homologous to the IE-1 promoter is used. More preferably, an even weaker promoter is used. A deletion mutant of the IE-1 promoter, the ΔIE-1 promoter, has about 20% of the transcriptional activity of that IE-1 promoter. The ΔIE-1 promoter sequence is: AATAAACGATAACGCCGTTGGTGGCGT-GAGGCATGTAAAAGGTTACATCATTAT CTTGT-TCGCCATCCGGTTGGTATAAATAGACGT-TCATGTTGGTTTTTGTTTCAGT TGCAAGTTGGCTGCGGCGCGCGCAGCACCTTTG (SEQ ID NO:1). The PCR primers that can be used to conveniently obtain the ΔIE-1 promoter in a form suitable for subcloning are: 5'-gcgcagatctAATAAACGATAACGCCGTTGGTGGC-3' (SEQ ID NO:2) and
5'-gtacgcggccgCAAAGGTGCTGCGCGCGCCGCAGC-3' (SEQ ID NO:3), where the sequences in capital letters indicate sequences within the ΔIE-1 promoter. Preferably, a promoter substantially homologous to the ΔIE-1 promoter is used. In respect to promoters, a homology of at least 50%, 60%, 70%, preferably 80%, more preferably 90% or more, is considered to be a substantially homologous promoter.

A Kozak-like sequence can be introduced in the region of the initiator amino acid of Rep78. Kozak, Cell (1986) supra and Kozak, *J. Cell. Biol.,* (1989) supra. By "Kozak-like" is meant an altered Kozak sequence. For example, a C to G mutation can be introduced at nucleotide position 4 of the coding sequence. It is generally expected that purines, especially guanidine, at positions −3 and +4 of the coding sequence improve translational expression. This particular modification, the C to G at position 4, may be specific for AAV2 Rep78 protein, but the principle can be applied easily to other AAV serotypes.

In mammalian-cell produced AAV, the best yield of "full" virions (i.e., viral particles incorporating an AAV genome), that are fully functional and can, for example, target the nucleus, is obtained when all three VP proteins are expressed, and they are at a stoichiometry approaching 1:1:10 (VP1:VP2:VP3). The regulatory mechanisms that allow this controlled level of expression include the production of two mRNAs, one for VP1, the other for VP2 and VP3, produced by differential splicing.

The splicing event required to produce AAV is not properly reproduced in the insect cell. In accordance with one embodiment, the VP coding region is operably linked to a promoter without the region upstream of the VP coding sequence normally found in wild-type AAV. Furthermore, optionally, one or two single point mutations can be introduced to inactivate the acceptor splicing element of the second splicing event which forms a second VP mRNA containing the VP2 and VP3 coding regions in expression of wild-type VP in mammalian cells. See also FIG. 1. For AAV2, the mutations of a T to A at position 21 of the coding sequence and/or an A to C at position 24 of the coding sequence of the VP1 coding nucleotide sequence were designed to remove any such potential splicing event. This resulted in a nucleic acid which is transcribed into a mRNA for translation into all three VP proteins. In accordance with a preferred embodiment, the VP promoter is the polh promoter. See also FIG. 1.

A further optional modification was shown to increase the expression of VP1. This consisted of the substitution of the nucleotide sequence immediately upstream of VP1 with a particular nine nucleotide sequence and the change of the initiator (first) codon of VP1 from methionine to threonine by an T to C mutation at position 2 of the coding nucleotide sequence. The nine nucleotide sequence is: 5'-CCTGTTAAG-3' (SEQ ID NO:4).

It is possible to employ variations of this sequence, i.e., by using a sequence with substantial homology to the nucleotide sequence. For example, a sequence introduced upstream of VP1 which is at least 60%, preferably 70%, more preferably 90% homologous to the nine nucleotide sequence of SEQ ID NO: 4 will help increase expression of VP1, such that a satisfactory stoichiometry between VP1, VP2, and VP3 is achieved.

For the AAV2 serotype, one other modification was shown to be potentially useful, i.e., the elimination of an out-of-frame ATG, by a T to C mutation at position 12 of the VP1 coding frame. Elimination of possible false start sites for translation of VP1 of other serotypes will be well understood by an artisan of skill in the art.

The various modifications of the wild-type AAV sequences for proper expression in insect cells is achieved by application of well-known genetic engineering techniques. Furthermore, numerous publications describe such techniques. See, for example, Richard (1995), supra; O'Reilly et al. (1994), supra; and Maniatis (1982), supra. Various further modifications of VP coding regions are known to the skilled artisan which could either increase yield of VP and virion or have other desired effects, such as altered tropism or reduce antigenicity of the virion. These modifications are within the scope of the present invention.

In accordance with the invention, an insect cell-compatible vector comprising at least one of the first to fourth nucleotide sequences of the invention is provided. In accordance with a preferred embodiment, the vector comprises a nucleotide sequence encoding a Rep78 or Rep68 gene operably linked to a ΔIE-1 promoter and a Kozak-like expression control sequence. In accordance with another preferred embodiment, the insect cell-compatible vector comprises an ORF comprising nucleotide sequences encoding AAV VP1, VP2, and VP3 capsid proteins operably linked to at least one expression control sequence comprising a nine nucleotide sequence of SEQ ID NO:4 or a nucleotide sequence substantially homologous to SEQ ID NO:4, upstream of the initiation codon of the nucleotide sequence encoding AAV VP1 capsid protein, and a C at position 2 of the nucleotide sequence encoding AAV VP1 capsid protein. Preferably, the AAV VP1, VP2 and VP3 capsid proteins are from AAV2 and the nucleotide sequence encoding VP1 comprises at least one modification selected from a C at nucleotide position 12, an A at nucleotide position 21, and a C at nucleotide position 24.

In accordance with the invention, an insect cell comprising at least one of a first nucleotide sequence comprising at least one AAV ITR nucleotide sequence, a second nucleotide sequence comprising an ORF comprising nucleotide sequences encoding AAV VP1, VP2, and VP3 capsid proteins operably linked to at least one expression control sequence for expression in an insect cell, a third nucleotide sequence comprising a Rep52 or a Rep40 coding sequence operably linked to at least one expression control sequence for expression in an insect cell, and a fourth nucleotide sequence comprising a Rep78 or a Rep68 coding sequence operably linked to at least one expression control sequence for expression in an insect cell is provided. Preferably, the fourth nucleotide sequence comprises a Kozak-like expression control sequence. Also preferably, the fourth nucleotide sequence comprises an expression control sequence selected from the IE-1 promoter, a promoter substantially homologous to the IE-1 promoter, a ΔIE-1 promoter, or a promoter substantially homologous to an ΔIE-1 promoter.

The first nucleotide sequence in the insect cell can comprise two AAV ITR nucleotide sequences and at least one nucleotide sequence encoding a gene product of interest for expression in a mammalian cell between the two AAV ITR nucleotide sequences. At least one of the first, second, third and fourth nucleotide sequences can be stably integrated in the insect cell.

In accordance with another aspect of the invention, a recombinant AAV is provided comprising a VP1 capsid protein comprising threonine at amino acid position 1. For example, an rAAV comprising a VP1 capsid protein comprising threonine is produced in the insect cell when the second nucleotide sequence present in the cell was modified at position 2 of the VP1 coding sequence. The initiation codon is now ACG and it translates into threonine.

In another aspect, the invention provides a method of producing a parvoviral genome in an insect cell. In the method, one or more insect cell-compatible vectors are introduced to an insect cell, which vector or vectors collectively comprise a first nucleotide sequence that includes at least one parvoviral ITR, a second nucleotide sequence comprising an AAV Rep52 or Rep40 coding sequence operably linked to at least one expression control sequence for expression in an insect cell, and a third nucleotide sequence comprising an AAV Rep78 or Rep68 coding sequence operably linked to at least one expression control sequence for expression in an insect cell. After introducing the vector or vectors to the insect cell, the insect cell is maintained under conditions such that a parvovirus genome is produced therein. The parvoviral genome can be any nucleic acid that (1) comprises 5' and 3'ITRs from or having substantial identity (e.g., at least about 70% identity, preferably at least about 80% identity, more preferably at least about 90% identity, or more (e.g., about 95–100% identity)) to AAV 5' and 3'ITRs, respectively, and (2) is capable of replicating in the insect cell upon the introduction of the one or more vectors. Preferably, the parvoviral genome further includes Rep sequences or homologous sequences. The parvovirus can be any suitable member of the Parvovirinae. Desirably, the parvovirus infects mammals. In a more preferred aspect, the parvovirus is a dependovirus. In a particularly preferred aspect, the dependovirus is a human or simian AAV. The parvovirus genome produced in the insect cell can include wild-type and/or modified ITRs, Rep sequences, and VP sequences, as well as one or more additional nucleotide sequences (e.g., one or more transgenes).

EXAMPLES

The present invention, thus generally described, will be understood more readily by reference to the following examples, which are provided by way of illustration and are not intended to be limiting of the present invention.

Example 1

This example demonstrates that AAV vector genome can replicate in insect cells when Rep protein is supplied in trans.

A recombinant baculoviral vector comprising the Rep78 ORF of AAV2 was produced and used to infect Spodoptera frugiperda Sf9 cells ($1 \times 10^7$) that had been co-infected at a multiplicity of infection (moi) of 5 with a recombinant baculoviral vector which comprises two AAV2 ITRs flanking a GFP open reading frame (pAAV2GFP) and which was produced as follows. A modified GFP gene was excised from pEGFP1 (Clontech) by digestion of the plasmid DNA with Nco I and Not I, and the resultant fragment was cloned into the Nco I-Not I site of pTriEx-1 (Novagen, Madison, Wis.). The resulting plasmid was digested with Rsr II and Msc I, blunt-ended, and the 1.1 kb fragment was inserted into a cytomegaloviral (CMV) expression plasmid, which expresses GFP in mammalian or insect cells by the CMV or p10 promoter. The entire GFP expression cassette was digested with Not I and subcloned between ITRs in an AAV2 vector-plasmid (pAAV2GFP). The AAV2 GFP vector portion was excised from pAAV2GFP by digestion with Hind III and Ssp I, blunt-ended, and inserted into the Eco105 I-Ecl136 II site of pFBHTb (Life Technologies, Rockville, Md.) producing pFBGFPR. pFastBacDual (pFBDVPm11 and pFBDLSR) (Life Technologies) and pFBGFPR were used to produce recombinant baculoviral vectors with the BAC-TO-BAC Baculovirus Expression System (Life Technologies).

At three days post-infection, extra-chromosomal DNA was isolated, resolved on a 1% agarose-TAE gel, transferred to nylon membrane, and hybridized with a radiolabeled probe for GFP. Dpn I-digested DNA from 293 cells transfected with pAAV2GFP alone or with pAAV2GFP and a plasmid comprising AAV and adenoviral helper genes (pDG) served as controls.

The cultures that were transfected with pAAV2GFP alone or with pAAV2GFP and pDG showed only the input recombinant baculoviral genome. However, monomeric, dimeric, trimeric and tetrameric forms of the GFP-AAV2 vector were detected when the Sf9 cells were co-infected with the recombinant baculoviral vector expressing AAV2 Rep. The GFP-probe specific bands corresponded in size to the "rescued" AAV genomes. The AAV2 ITRs served as Rep-dependent origins of DNA synthesis and were excised from the plasmid or baculoviral vector. There was a net synthesis of the rescued DNA, as determined based on comparison of the relative strengths of the signals obtained with and without Rep. In fact, the increased presence of GFP-containing DNA was clearly evident as fluorescent bands on an ethidium bromide-stained gel. The pattern of GFP-specific bands obtained in 293 cells co-transfected with pAAV2GFP and pDG was qualitatively similar to that obtained with the Sf9 cells. These results demonstrate that Rep78 functions as a replication initiator protein on DNA substrates that contain AAV ITRs, and the AAV vector genome can replicate in insect cells when Rep protein is supplied in trans.

Example 2

This example describes the design of genetic constructs for balanced expression of AAV functions in insect cells.

FIG. 1 represents a genetic and a transcriptional map of the wild-type AAV genome. The top line represents the genome and the transcriptional promoter sites. Black boxes indicate the ITRs, which are the origin of AAV replication in a mammalian setting. The left half of the AAV genome codes for four overlapping nonstructural proteins, Rep78, Rep68, Rep52, and Rep40. The unspliced and spliced transcripts from the p5 promoter are translated to Rep78 and Rep68. The Rep52 or Rep40 is synthesized from the p19 transcript by alternate splicing. Balanced expression of Rep78 and Rep52 is necessary for generating high titers of AAV vectors in 293 cells. Yields of vector are adversely affected when Rep78 is present at super-optimal levels.

In order to limit expression of Rep78 in Sf9 cells, the promoter for the immediate early 1 (IE-1) gene of Orgyia pseudotsugata nuclear polyhedrosis virus was used. To limit expression of Rep78 even further, the IE-1 promoter was partially deleted, by limiting the promoter region to that portion of the IE-1 promoter residing within the Bgl II-Not I 163 fragment (ΔIE-1). The ΔIE-1 promoter functioned at approximately 20% of the intact IE-1 promoter level.

The AAV2 p78 Rep gene was amplified by polymerase chain reaction (PCR) from a plasmid containing AAV2 Rep and cap genes using the primers 5'-GTTACTCTTCAGCCATG GCGGGGTTTTACGAGATTG-3' (SEQ ID NO:5) and 5'-AGTTACTCTTCATCAGAGAGAGTGTCCTCGAGC C-3' (SEQ ID NO:6) and PfuTurbo DNA polymerase (Stratagene, La Jolla, Calif.). The C at position 4 of the Rep gene was mutated to G (underlined) to introduce a Kozak-like expression control sequence at the translation initiation site. Kozak (1986), supra; and Kazak (1989), supra. The resulting Rep ORF was inserted into pCR-Blunt II-TOPO (Invitrogen, Carlsbad, Calif.), cut out with Not I and Spe I (blunt), and then subcloned into the Not I-Avr II (blunt) site of pBAC-1 (Novagen), (pBACRep). The IE-1 promoter was PCR-amplified from pIZT/V5-His (Invitrogen) using primers 5'-GCGCAGATCTAATAAACGATAACGCCGTTG GTGGC-3' (SEQ ID NO:2) and 5'-GTAC GCGGCCGCAAAGGTGCTGCGCGCGCC GCAGC-3' (SEQ ID NO:3) (Bgl II and Not I sites are underlined). The resulting 163 bp fragment was treated with Bgl II and Not I, and inserted into the Bgl II-Not I site of pBACRep (pBACΔIERep). pBACΔIERep was digested with Eco RV and Not I, blunt-ended, and self-circularized to remove an unnecessary ATG codon upstream of the Rep coding nucleotide sequence. The AAV2 Rep expression cassette was cut out by digestion with Bgl II and Sph I, blunt-ended, and inserted into the Nco I-Bam HI (blunt) site of pFastBacDual (Life Technologies) (pFBLR).

The AAV2 Rep52 gene was obtained from pCMVRep52 by digesting with Nco I and Acc65 I and inserted into the Nco I-Acc65 I site of pFBHTa (Life Technologies). The resulting plasmid was treated with Rsr II and Ehe I, blunt-ended, and self-circularized. The AAV2 Rep52 cassette was cut out by digesting with BstZ17 I and Xho I (blunt) and inserted into the Pvu II site of pFBLR resulting in pFBDLSR.

In mammalian cells, the capsid proteins, VP1, VP2, and VP3 are synthesized from two spliced mRNAs arising from the p40 promoter (FIG. 1). One message is translated into VP1, while another transcript encodes VP2 and VP3. The naturally occurring initiation codon for VP2 is ACG, which is poorly utilized, resulting in ribosome scanning through to the VP3 initiation codon (AUG). The alternate usage of two splice acceptor sites and the poor utilization of the ACG initiation codon for VP2 are responsible for the stoichiometry of VP1, VP2, and VP3 in AAV2-infected mammalian cells and mirrors the protein ratio in the capsids, 1:1:10. The AAV cap intron is not spliced in insect cells.

To generate empty AAV capsids in Sf9 cells with similar stoichiometry to capsids produced in mammalian cells, a mutated AAV2 VP gene was used, in which the initiation codon for VP1 was changed to ACG. Furthermore, the three capsid proteins were engineered to be expressed from a single expression cassette by the removal of the acceptor splice site. However, the level of VP1 expression and incorporation into empty virus-like particles was much lower than VP2 and these particles transduced cells poorly. VP2 was expressed at the appropriate levels relative to VP3, despite the lack of a typical initiation codon. Several permutations of the sequence surrounding the VP2 ACG codon were tested for the ability to enhance the level of translated VP1 protein. One construct incorporating a 9-nt element derived from upstream of the VP2 ACG codon was introduced at a similar position relative to VP1. This cassette produced VP1 at similar levels to VP2 without affecting VP3 expression, a situation similar to expression in 293 transfected cells.

In particular, the AAV2 VP gene was amplified by PCR using primers 5'-cgcggatcctgttaagACGGCTGCCGA CGGTTATCTACCCGATTGGCTC-3' (SEQ ID NO:7) and 5'-gcTTACAGATTACGAGTCAGGTATCTGG-3' (SEQ ID NO:8). The sequence corresponding to the VP ORF is capitalized and bases mutated relative to wild-type sequence are underlined. The PCR-amplified VP gene had the initiation codon of the VP1 mutated to ACG to reduce its translation efficiency. An out-of-frame ATG, which had diminished the translation of VP2 and VP3 located downstream, was modified by changing the T to C at nucleotide position 12.

The splice acceptor site downstream of the AAV2 VP1 initiation codon was destroyed to prevent possible splicing of mRNA by substituting A and C for T at position 21 and A at position 24, respectively. The amplified VP gene was cloned into a CMV expression plasmid and was tested for the expression of VP polypeptides in 293 cells. Then, the VP gene was digested with Bam HI and subcloned into the Bam HI site of pFBDVPm11 (Life Technologies).

Wild-type AAV was grown in 293 cells in Dulbecco's modified Eagle's medium (DMEM)/F12 (1:1) (Life Technologies) supplemented with 10% fetal calf serum (FCS). The Sf9 cells (Life Technologies) containing the three baculoviral vectors were grown at 27° C. in shaker flask cultures containing Sf-900 II SFM (Life Technologies) supplemented with 10% FCS.

Expression of AAV2 Rep78/52 and VP1, VP2, and VP3 was assayed. Five micrograms (293 cells) of protein in total cellular lysate were or 1 µg (Sf9 cells) of protein in total cellular lysate was resolved on an SDS Tris-glycine 10% polyacrylamide gel. Anti-Rep antibody was used to detect Rep78 and Rep52, and anti-VP antibody was used to detect VP1, VP2, and VP3. Wistube et al., J. Vir. 69:5311–19 (1995); and Wistube et al., J. Vir. 71:1341–52 (1972). The antibodies are commercially available from Research Diagnostics, Inc., Flanders, N.J.

Cells were lysed in 1× SDS sample buffer and electrophoresed on an SDS Tris-glycine 10% polyacrylamide gel. The separated proteins were transferred to polyvinylidene difluoride (PVDF) membrane, incubated with a monoclonal anti-Rep antibody (303.9, Research Diagnostics, Inc., Flanders, N.J.) or a polyclonal anti-VP antibody (Research Diagnostics, Inc.), and then incubated with a secondary anti-mouse or anti-rabbit immunoglobulin G labeled with horseradish peroxidase. Chemiluminescent signals were detected by SuperSignal West Pico Chemiluminescent Substrate (Pierce Chemical Co., Milwaukee, Wis.). Qualitatively similar ratios of AAV2 Rep and VP proteins were obtained in the 293 and Sf9 cells. These results demonstrate that the genetic constructs enable balanced expression of AAV functions in insect cells.

Example 3

This example demonstrates that rAAV can be produced in insect cells.

Sf9 cells were infected with three recombinant baculoviruses: GFPBac, RepBac, and VPBac. RepBac harbors AAV2 Rep78 and Rep52 expression cassettes. The AAV2 Rep78 expression cassette is under the control of a ΔIE-1 and Rep52 is expressed by the polyhedron (polh) promoter. VPBac expresses the AAV2 capsid proteins VP1, VP2, and VP3 under the transcriptional control of polh. The ATG codon of AAV2 VP1 was mutated to ACG, enabling the expression of all three VP polypeptides from one transcript, without splicing of mRNA. GFPBac carries a GFP vector genome. The CMV or p10 promoter drives GFP expression in mammalian cells or insect cells. The whole expression cassette is flanked by AAV2 ITRs. See FIG. 2, which is a genetic map of recombinant baculoviruses employed to produce rAAV in insect cells. (PA is the polyA signal).

After three days, the infected cells were lysed and fractionated by CsCl density gradient centrifugation. Sf9 cells ($1 \times 10^7$) infected with three recombinant baculoviruses were subjected to ultracentrifugation. Twelve 1-ml fractions were collected and a portion of each fraction was analyzed by Western blotting using an anti-VP antibody. Two peaks were observed. One peak had a buoyant density of 1.37 or 1.40 g/cm$^3$, which corresponds to the density of wild-type AAV or rAAV2 vectors produced in mammalian cells. The other peak was at 1.33 g/cm$^3$, which is the density of empty capsids. Densitometry of bands revealed that approximately 15% of the total VP polypeptides produced was utilized for assembly of filled capsids. A control experiment with 293 cells producing an AAV vector showed that the packaged to unpackaged capsid ratio is similar. The analysis of Sf9 cells infected with VPBac alone showed production only of the lighter fractions with peak density of 1.33 g/cm$^3$. The denser fractions were collected and purified by heparin column affinity chromatography. The genomic titer was determined by real-time PCR using GFP-specific primers and linearized GFP plasmid standards. Western analysis of $10^9$ vector genome equivalents produced in 293 cells or Sf9 cells processed in parallel showed VP1:VP2:VP3 stoichiometry to be similar. An electron micrograph of the rAAV2 produced in insect cells showed spherical or icosahedral particles of approximately 25 nm in diameter, which is a typical morphological feature of AAV.

Cumulatively, these experiments demonstrate that an AAV particle comprising an AAV genome can be produced in insect cells comprising vectors expressing the indicated complement of AAV functions.

Example 4

This example demonstrates that rAAV produced in Sf9 and 293 cells are functionally equivalent.

To compare the biological properties of the GFP vector produced in invertebrate cells to that produced in mammalian cells, 293 cells were infected with rAAV2-GFP produced in Sf9 or 293 cells at doses ranging from $1 \times 10^2$ to $3 \times 10^3$. The number of GFP-positive 293 cells after infection with the insect-cell-produced GFP vector was shown to be comparable to the number of GFP-positive 293 cells after infection with the GFP vector produced in 293 cells.

To demonstrate that the presence of GFP in 293 cells is mediated by rAAV2-GFP, 293 cells ($1 \times 10^5$ per well in a 12-well plate) were pre-incubated for 30 minutes at 37° C. with A20 monoclonal antibody (1.2 µg/ml; Research Diagnostics, Inc.), which is capable of neutralizing rAAV2 as well as wild-type AAV2, or anti-hemagglutinin (HA) mouse monoclonal antibody (Santa Cruz Biotechnology, Inc., Santa Cruz, Calif.) and further incubated for two days. When 293 cells were preincubated with the A20 antibody, rAAV2-GFP produced in 293 cells or in Sf9 cells failed to transduce 293 cells, whereas the anti-HA antibody did not interfere with transduction by either rAAV2-GFP.

A primary co-receptor for AAV2 (and AAV2 vectors) is heparan sulfate proteoglycan, which is required for efficient uptake of AAV2 into target cells. Competition essays with heparin also were performed by pre-incubating 293 cells with 0, 2 or 20 µg/ml heparin (Sigma-Aldrich, St. Louis, Mo.) and infecting the 293 cells with AAV vectors. An analog of heparan sulfate, heparin has been shown to inhibit transduction with AAV vector at the concentration of 5 µg/ml. It was observed that heparin inhibited GFP vector-mediated transduction of 293 cells in a concentration-dependent manner, irrespective of whether the GFP vector was produced in Sf9 or 293 cells.

Example 5

This example demonstrates that rAAV can be produced in high titers in insect cells.

AAV vectors were produced in mammalian cells by transfecting 293 cells with pAAV2GFP and pDG by the calcium phosphate precipitation method. pDG harbors AAV Rep and cap genes as well as adenoviral E2A, E4ORF and VARNA genes. Two days following transfection, AAV vectors were purified as described below. AAV vectors were produced in Sf9 insect cells by infecting $2 \times 10^6$ cells/ml in suspension culture with recombinant baculovirus at a moi of 5. At three days post-infection, the infected cells were pelleted by centrifugation and lysed in a buffer of 50 mM Tris-HCl (pH 8.4), 50 mM NaCl, 2 mM $MgCl_2$, 1% deoxycholic acid, 0.5% 3-[(3-cholamidopropyl) dimethylammonio]-1-propanesulfonate (CHAPS), and 60 U/ml of Benzonase (Novagen). After incubation for 30 min at 37° C., the concentration of NaCl in the cell lysate was adjusted to 150 mM and incubated for an additional 30 min. Solid CsCl was added to obtain a final density of 1.36 g/cm³. The cell lysate was centrifuged at 38,000 rotations per minute (r.p.m.) for 24 hr at 21° C. using a SW41Ti rotor (Beckman Coulter, Fullerton, Calif.). Aliquots of gradient fractions were dialyzed against phosphate-buffered saline (PBS) (1.34 mM KCl, 0.74 mM $KH_2PO_4$, 69 mM NaCl, 4.03 mM $Na_2HPO_4$) and analyzed by SDS-PAGE and Western blotting with anti-VP antibody (see below). The fractions containing AAV vectors were collected and dialyzed against 0.5× PBS with 1 mM $MgCl_2$ and incubated with 28 U/ml of Benzonase for 1 hr at 37° C. to digest any residual DNA. The dialysate was loaded onto a column filled with cellufine heparin (Millipore, Bedford, Mass.) and washed with 10 column volumes of 0.5× PBS and with 10 column volumes of 20 mM Tris-HCl (pH 8.0) and 0.25 M NaCl. Bound AAV vectors were eluted with 20 mM Tris-HCl (pH 8.0) and 0.5 M NaCl. The eluate was dialyzed against PBS/2 mM $MgCl_2$, aliquoted, and stored at −80° C. The titer of AAV vector was determined by real-time PCR on an iCycler (Bio-Rad Laboratories, Hercules, Calif.). Briefly, proteinase K-treated rAAV was serially diluted and PCR-amplified using SYBR green master mix (Applied Biosystems, Foster City, Calif.) with primers specific to the GFP gene. Linearized pAAV2GFP was employed as a copy number standard. The cycling conditions were: 95° C. for 3 min, followed by 35 cycles of 95° C. for 30 sec, 60° C. for 30 sec, and 72° C. for 30 sec. Transducing units were determined by infecting 293 cells with rAAV-GFP at 100 vector genomes per cell and counting positive cells under a fluorescent microscope. This was corroborated by flow cytometric analysis of transduced cells.

Table 1 summarizes the yield of AAV vector recovered from 293 cells in twenty 175-cm² flasks (a total of $4 \times 10^8$ cells) or from the same number of insect cells in 200 ml suspension culture by three independent preparations. The yield from 293 cells was $5 \times 10^3$ GFP-vector genomes per cell following CsCl banding and subsequent heparin affinity chromatography. In contrast, Sf9 cells generated approximately $5 \times 10^4$ encapsidated vector genomes per cell, a 10-times higher yield than 293 cells. The vector genomes to transducing unit ratio (vg/TU) of Sf9-produced rAAV GFP was 1300, while that of 293-produced rAAV was 3,000, which suggests that the transduction efficiency of GFP vector produced in insect cells is equivalent to that of GFP vector produced in mammalian cells. To check for the presence of contaminating recombinant baculoviruses in the AAV vector stocks, aliquots of the stocks were plaque assayed. GFP-positive cells or plaques were below the detection limit.

TABLE 1

Comparison of rAAV yield between two methods[a].

| | after CsCl handing[b] | | after chromatography[b] | | |
|---|---|---|---|---|---|
| | total yield | per cell | total yield | per cell | vg/TU[c] |
| 293 cells 20 175-cm² flasks | $1.5 \times 10^{12}$ | $3.8 \times 10^3$ | $2.0 \times 10^{12}$ | $5.0 \times 10^3$ | 3033 |

TABLE 1-continued

Comparison of rAAV yield between two methods[a].

| | after CsCl handing[b] | | after chromatography[b] | | |
|---|---|---|---|---|---|
| | total yield | per cell | total yield | per cell | vg/TU[c] |
| Sf9 cells 200 ml culture | $3.7 \times 10^{13}$ | $9.3 \times 10^4$ | $1.8 \times 10^{13}$ | $4.5 \times 10^4$ | 1344 |

[a]293 or Sf9 cells ($4 \times 10^8$) were used for rAAV production in each of three independent experiments.
[b]Samples were taken at each step and used for titer determination.
[c]vector genomes/transducing unit.

The AAV vector produced in insect cells was shown to have similar physical and biochemical properties to that produced in mammalian cells. In addition, the titer of the AAV vector obtained in insect cells was one of the highest. Ten liters of insect cell culture is estimated to produce an AAV vector equivalent to $10^{15}$ vector genome, a titer that would be required for a clinical study. This robust production system based on baculovirus greatly simplifies the vector production process and facilitates the studies of applications of AAV vectors. Thus, this example evidences that rAAV can be produced in higher titers in insect cells as compared to mammalian cells.

Example 6

This example demonstrates how rAAV is produced utilizing a three vector system comprising a baculoviral vector containing a chimeric ITR.

Production of rAAV using a three vector system where one vector contains a chimeric ITR, a second vector contains the Rep protein equivalent NS-1, and a third vector contains the VP structural proteins is as described in Example 3. However, the baculoviral vector containing two AAV ITRs (GFPBac) is replaced with a baculoviral vector containing at least one chimeric ITR (see FIG. 5C) where the nucleotide sequence representing the AAV2 Rep binding site and AAV2 nicking site is replaced with nucleotide sequence representing the NS-1 binding site (GAC four repeat) and NS-1 nicking site (G*TATTG) and the baculoviral vector which will allow for expression of the Rep78 and Rep52 proteins (RepBac) is replaced with a vector which contains the nucleotide sequences which allow for the expression of the Rep protein equivalent NS-1, optionally Rep78 or Rep68 and Rep52 protein.

Example 7

This example describes the production of recombinant AAV particles comprising AAV1 capsid proteins in insect cells.

A modified AAV1 VP gene, designed to provide VP expression in insect cells at levels similar to the levels of VP expression observed in mammalian cells, was generated by amplifying an AAV1 VP gene (GenBank Accession No. NC_002077) with the PCR primers 5'-CGCGGATCCTGTTAAAGACGGCTGCCGACGGTT TCTACCCGATTGGCTC-3' (SEQ ID NO:9) and 5'-GCTTACAGGGGACGGGTAAGGTA-3' (SEQ ID NO:10). The modified AAV1 VP gene PCR product possesses similar features as the modified AAV2 VP gene described in Example 2 (i.e., (1) the initiation codon of the VP1 was mutated to ACG to reduce its translation efficiency, (2) an out-of-frame ATG codon was eliminated by replacing the thymine at nucleotide position 12 of the amplified VP gene with a cytosine and (3) the splice acceptor site downstream of the VP1 initiation codon was destroyed by replacing the thymine at position 31 with an adenine and replacing the adenine at position 24 with a cytosine, such that the modified AAV1 VP gene encodes the three AAV1 capsid proteins as a single expression cassette).

Figure 6:
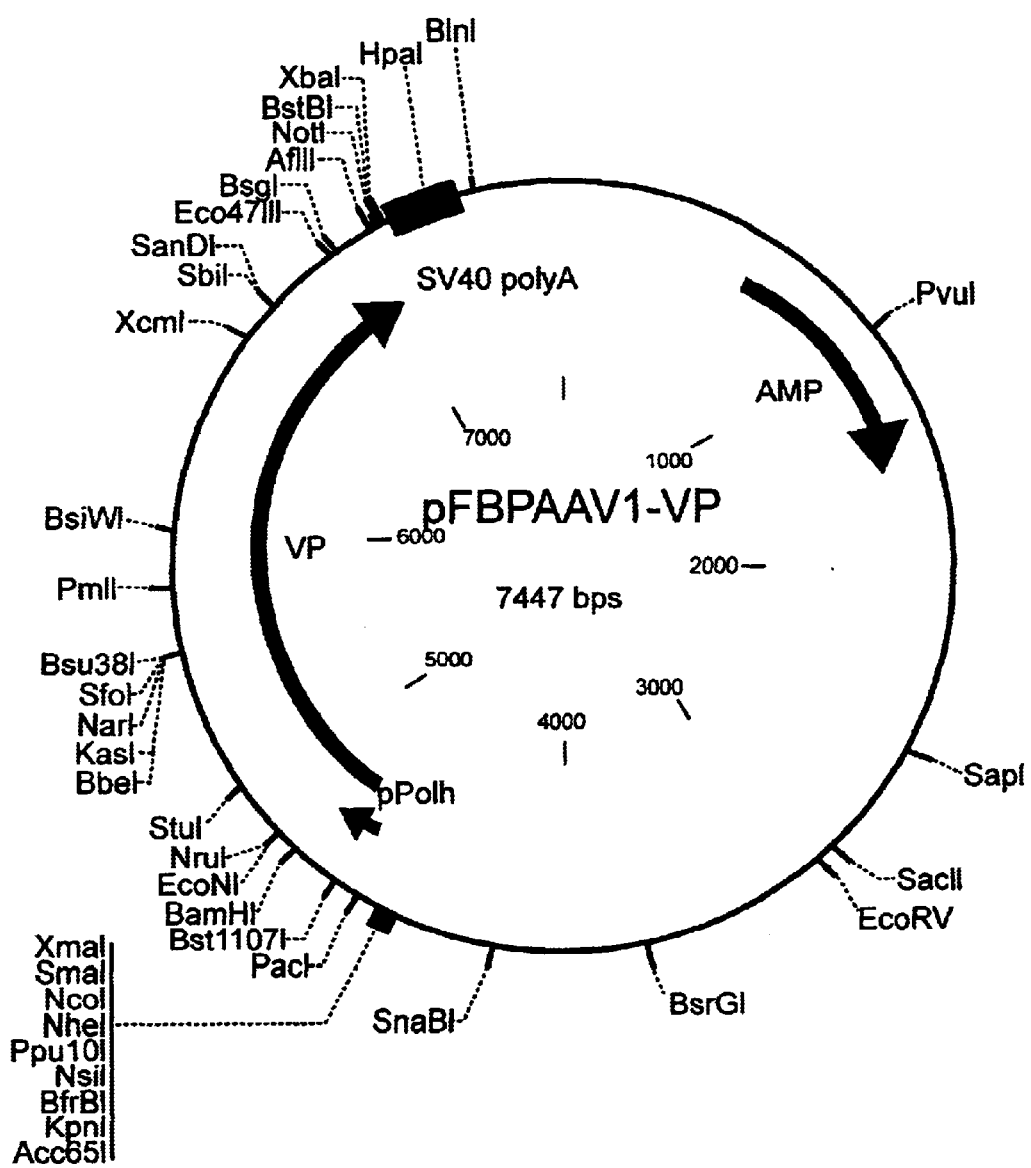
FIG. 6 is a genetic map of an exemplary recombinant vector comprising a modified AAV1 VP gene, which vector used for the production of rAAV1 and AAV1-pseudotyped vectors in insect cells.

The modified AAV1 VP gene PCR product was digested with BamHI and subcloned into the BamHI site of pFBD-VPm11 to generate vector pFBDAAV1-VP (SEQ ID NO:11), a genetic map of which vector is shown in FIG. 6.

Recombinant baculovirus vectors comprising the mutant AAV1 VP gene (Bac-AAV1 VP) were produced from pFBDAAV1-VP using the BAC-TO-BAC Expression System, following the manufacturer's protocol. Recombinant baculovirus comprising an AAV2 p78 Rep/Rep52 sequence (Bac-AAV2 LSR) and recombinant baculovirus comprising an AAV2-ITR/GFP/AAV2-ITR sequence (Bac-AAV2 GFPR), as described in Example 2, also were prepared.

Seven cultures of $2 \times 10^6$ cells/mL (500 mL) Sf9 cells (Life Technologies) were co-infected with Bac-AAV1 VP, Bac-AAV2 LSR, and Bac-AAV2 GFPR, each at a moi of 5. The baculovirus-infected Sf9 cells were grown at 27° C. in shaker flask cultures containing Sf-900 II SFM supplemented with 10% FCS. At three days post-infection, the infected cells were pelleted and lysed by detergent as described in Example 5. After incubation for 30 min at 37° C., the concentrations of NaCl and CsCl were adjusted, as described in Example 5, and the cell lysate was centrifuged at 38,000 rotations per minute (r.p.m.) for 64 hr at 21° C. using a SW41Ti rotor. The Sf9 cell lysate fractions enriched for AAV vectors by the CsCl gradient centrifugation were collected, dialyzed against 0.5× PBS with 1 mM $MgCl_2$, and incubated with 28 U/ml of Benzonase for 1 hr at 37° C.

Quantitative real-time PCR was performed with a Bio-Rad iCycler to determine the titer of the rAAV2/1 vector according to standard techniques. Briefly, proteinase K-treated rAAV2/1 was serially diluted and PCR-amplified using SYBR green master mix with primers specific to the GFP gene under conditions specified in Example 5. Linearized pAAV2GFP was employed as a copy number standard.

The above-described technique was repeated an additional four times on different days from the first experiment. The results for the five experiments are presented in Table 2.

TABLE 2 rAAV2/1 vector genome yields in Sf9 cells as determined by quantitative RT-PCR

| Experiment # | Yield (vector genomes/cell) |
|---|---|
| 1 | $7 \times 10^4$ |
| 2 | $4 \times 10^4$ |
| 3 | $6.3–6.75 \times 10^4$ |
| 4 | $4 \times 10^4$ |
| 5 | $4 \times 10^4$ |

As shown in Table 2, the results of the RT-PCR assays indicate that an average of about $4 \times 10^4 – 7 \times 10^4$ chimeric rAAV2/1 genomes are produced per Sf9 cell. Thus, these results indicate that pseudotyped rAAV2/1 can be produced in insect cells at titers above the titers of rAAV2 in mammalian cells and comparable with the titer of rAAV2 produced in Sf9 cells (see Example 5 for comparison).

The transducing unit/vector genome ratio for the rAAV 2/1 vectors produced in the Sf9 cells was determined as described in Example 5. The rAAV2/1 vg/TU ratio for the insect cell-produced rAAV2/1 vectors was determined to be approximately $1\times10^3$, which ratio is similar to that observed for rAAV2 produced in Sf9 cells. Taking into account the order of magnitudes and standard deviation, the vg/TU ratios observed for 293 cell-produced rAAV2 and Sf9-cell produced rAAV2/1 also are relatively similar, indicating that the transduction efficiency of rAAV produced in insect cells is comparable to that of rAAV produced in mammalian cells.

The results of these experiments demonstrate that recombinant AAV comprising AAV1 capsid proteins can be produced at high titers in insect cells while retaining transduction efficiency comparable with AAV produced in mammalian cells.

Example 8

This example describes the production of rAAV 2/4 vector particles in insect cells using ITRs and Rep genes obtained from AAV2 and a modified VP gene derived from AAV4.

To obtain a modified AAV4 VP gene capable of expressing VP proteins in insect cells at levels similar to the expression levels associated with VP expression in mammalian cells, AAV4 VP (GenBank Accession No. NC_001829) was subjected to PCR amplification with the primers 5'-CGGATCCTGTTAAGACGGCTGACGGTTACCTTCC AGATTGGC-3' (SEQ ID NO: 12) and 5'-GTTATTACAGGTGGGTGAGGTAGCG-3' (SEQ ID NO: 13).

The resulting modified AAV4 VP gene PCR product possessed similar features to the modified AAV2 and modified AAV1 VP genes described in Examples 2 and 7, respectively (i.e., the AAV4 initiation codon was mutated to ACG to reduce translation efficiency; the splice acceptor site downstream of the VP1 initiation codon was destroyed; and the three capsid proteins were engineered to be expressed from a single initiation site).

Figure 7:
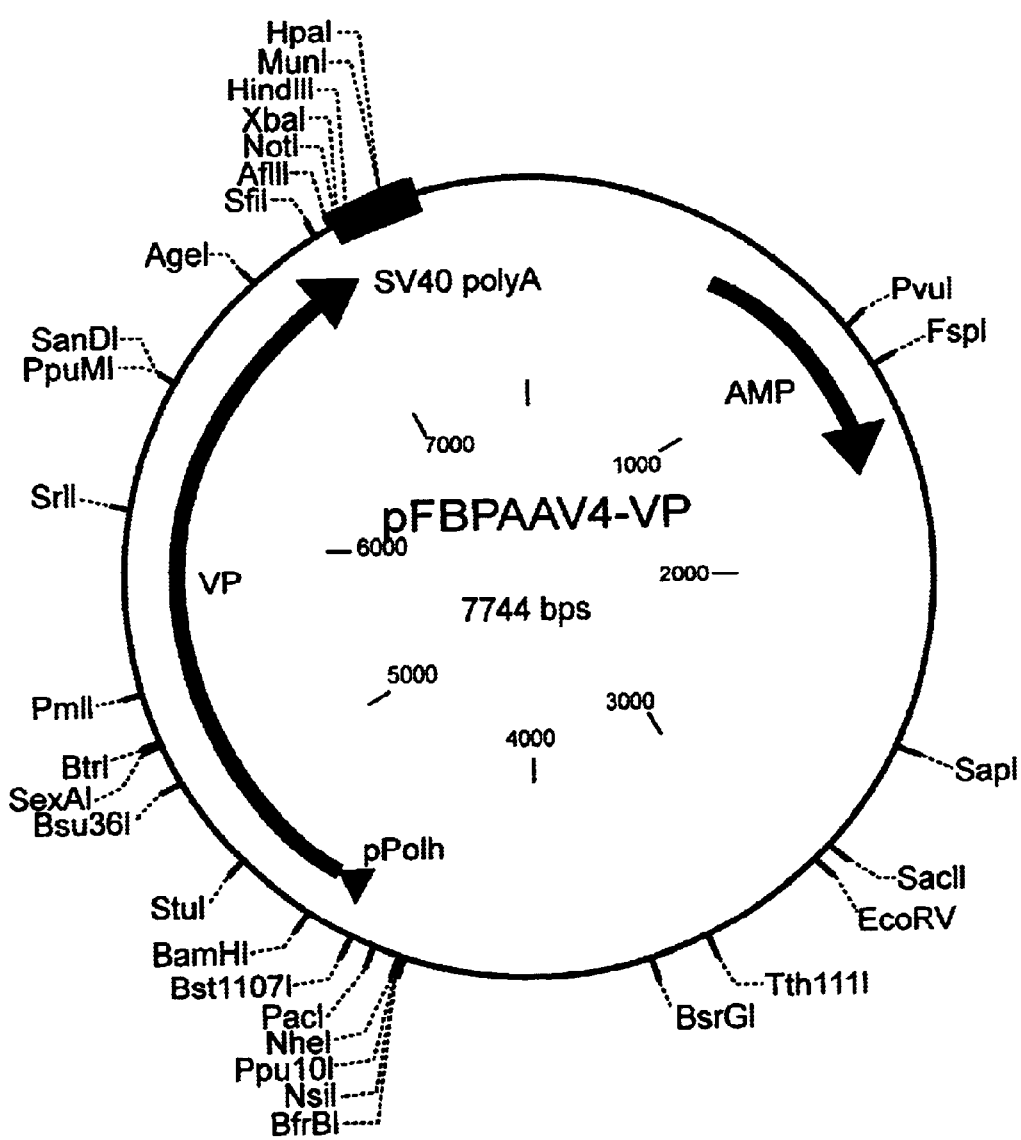
FIG. 7 is a genetic map of a representative recombinant vector comprising a modified AAV4 VP gene used for the production of rAAV4 and AAV4-pseudotyped vectors in insect cells.

The AAV4 modified VP PCR product was digested with BamHI and subcloned into the BamHI site of pFBDVPm11 to generate the vector pFBDAAV1-VP (SEQ ID NO:14), a map of which vector is shown in FIG. 7.

Recombinant baculovirus vectors comprising the mutant AAV4 VP gene (Bac-AAV4 VP) were produced from pFBDAAV4-VP using the BAC-TO-BAC Expression System. Cultures of $2\times10^6$ cells/mL ($4\times500$ µL) Sf9 cells were co-infected with Bac-AAV1 VP, Bac-AAV2 LSR, and Bac-AAV2 GFPR, each at a moi of 5. The infected cells were cultured, pelleted, and lysed, and AAV fractions collected from the lysate as described in Examples 5 and 7.

The experiment was repeated four additional times, under identical test conditions, on four different days. For each of the five experiments, quantitative real-time PCR was performed using a Bio-Rad iCycler to determine the titer of the rAAV2/1 vector as described in Examples 5 and 7. Linearized pAAV2GFP was employed as a copy number standard. The results of these experiments are provided in Table 3.

TABLE 3

| rAAV vector genome yields in Sf9 cells as determined by quantitative RT-PCR | |
|---|---|
| Experiment | Yield (vector genomes/cell) |
| 1 | $1 \times 10^4$ |
| 2 | $2.8 \times 10^2$ |

TABLE 3-continued

| rAAV vector genome yields in Sf9 cells as determined by quantitative RT-PCR | |
|---|---|
| Experiment | Yield (vector genomes/cell) |
| 3 | $2.1 \times 10^3$ |
| 4 | $2.8 \times 10^2$ |

The results of these real-time PCR assays indicate that $2.1\times10^3$–$2.8\times10^4$ rAAV2/4 genomes are produced per Sf9 cell.

These results demonstrate that rAAV comprising AAV4 capsid proteins can be produced at very high titers in insect cells. Indeed, these results indicate that the titer of rAAV2/4 produced in Sf9 cells is significantly higher than the titer of wild-type AAV2 produced in 293 cells under similar conditions as described in Example 5.

Example 9

This example illustrates the measurement of transduction efficiency of rAAV produced in insect cells.

COS cell cultures transduced with equivalent amounts of rAAV4 or rAAV2 are known to exhibit similar AAV transduction levels; however, other cell lines exhibit differential transducibility (Chorini et al., J. Virol. 71(9):6823–6833 (1997)). Recombinant AAV2 vectors are capable of efficient transduction of 293 cells (see, e.g., Example 5).

$4\times10^5$ COS-5 cells and 293 cells were transduced with $4\times10^7$ vg of the rAAV2/4 vector particles described in Example 8. The titer of the rAAV genomes in the transduced cells was determined by quantitative RT-PCR using a Bio-Rad iCycler according to manufacturer's instructions and as described in Examples 5 and 7.

Differential transduction efficiencies were observed for rAAV4/rAAV2 in 293 cells as compared to COS-5 cells. In the 293 cells, rAAV transduction was minimal, whereas COS-5 cells were transduced efficiently (i.e., at levels similar to previously observed rAAV4 and rAAV2 transduction levels in COS cells). Although exact quantitative differences could not be determined, the relative rAAV transduction efficiencies observed in the COS-5 and 293 cells differed by about 10–100× (i.e., about 1–2 logs). This result agrees with previous observations that rAAV4 particles exhibit different transduction levels of cells efficiently transduced by AAV2 other than COS cells.

The result of this experiment demonstrates that recombinant rAAV produced in insect cells retain the transduction characteristics associated with AAV particles having similar capsid proteins produced from mammalian cells. Specifically, the results of this experiment demonstrate that rAAV2/4 exhibit similar transduction characteristics as rAAV4 produced from mammalian cells. Consequently, the result of this experiment also confirms that the recombinant particles produced in Example 8 comprise AAV4 capsid proteins, rather than AAV2 capsid proteins.

Example 10

This example illustrates the development of modified VP sequences suitable for production of AAV in insect cells. More specifically, this example describes the identification of a modified AAV5 VP sequence suitable for producing AAV5 in insect cells in combination with suitable AAV5 Rep and ITR sequences.

A modified AAV5 Rep78/68-encoding sequence was generated by amplifying a wild-type AAV5 Rep78/68-encoding sequence (GenBank Accession No. AF085716) with the primers 5' CAGATCT ATGGCTACCTTCTATGAAGTCATTGTTCG-3' (SEQ ID NO:15) and 5'-TTATCACCAACTTCTTCCAACCAATCTGGAGG-3' (SEQ ID NO:17). A modified AAV5 Rep52/40 coding sequence was similarly generated by amplifying a wild-type AAV5 Rep52/40 sequence from the same strain using a 5' primer having the sequence 5'-GGAC ATGGCGCTCGTCAACTGGCTCGTGGAGCACG-3' (SEQ ID NO:16) and SEQ ID NO:17. The underlined ATG codons in these sequences indicate positions where the modified Rep sequences differs from the corresponding wild-type Rep sequences.

Figure 8:
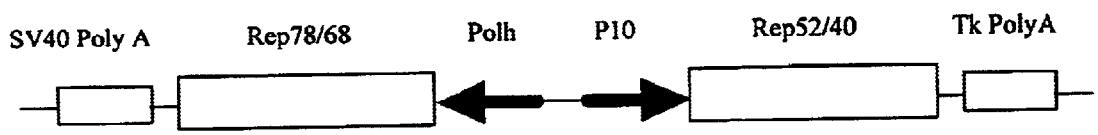
FIG. 8 and FIG. 9 are maps of representative vectors comprising modified AAV5 Rep and AAV5 VP sequence expression cassettes, respectively, which vectors are used in the production of rAAV5 in insect cells.

The modified Rep sequence PCR products were inserted into plasmid pFBD to generate a recombinant shuttle vector for the production of baculovirus vectors. Specifically, the modified AAV5 Rep78/68 PCR product was operably ligated to a Polh promoter and SV40 polyadenylation sequence and the modified AAV5 Rep52/40 sequence was similarly operably ligated to a p10 promoter and thymidine kinase (Tk) polyA sequence using standard techniques. The p10 and polh promoters and Rep sequences were oriented in opposite directions, such that a plasmid comprising a bidirectionaly-oriented dual expression cassettes was obtained. A genetic map of this plasmid, pFBD-AAV5-Rep5 cassette, is provided in FIG. 8.

To identify a suitable AAV5 VP sequence for producing AAV5 in insect cells, a wild-type VP sequence was amplified with primers selected to introduce modifications into the VP1 start codon and surrounding region in the resulting PCR product. Specifically, primers were selected and PCR amplifications performed with wild-type AAV5 VP (Accession No. AF085716) to produce six modified AAV5 VP sequences having one or more differences in the region of the VP1 start codon as compared to the wild-type AAV5 VP1 start codon and surrounding region, i.e., 5'-ATGTCTTTTGTTGATCACCCTCCAGA TTGGT-3' (SEQ ID NO: 18). The sequences of the six modified VP sequences so generated are set forth in Table 4.

Figure 9:
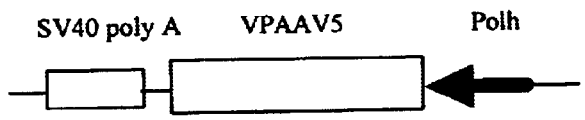

Each of these six PCR amplifications was performed such that the splice sites in the wild-type AAV5 VP sequence were eliminated in the resulting modified VP sequence. As such, each modified VP sequence PCR product included a single ORF encoding AAV5 VP1, VP2, and VP3. Additionally, each of the six modified VP PCR products was operably linked (ligated in frame) to a polh promoter and SV40 polyA sequence, using standard techniques, and the resulting VP expression cassette was inserted into plasmid pFBD, thereby generating plasmid pFBDVP-5 (see FIG. 9).

Using the BAC-TO-BAC system (described above), baculovirus vectors were produced from the pFBDVP-5 vectors. Similarly, a baculovirus vector comprising the modified AAV5 sequence was produced from plasmid pFBD-Rep5 cassette and a plasmid comprising the 5' and 3' AAV5 ITRs with a GFP reporter gene positioned between the ITR sequences.

To test the ability of the modified VP sequences to support production of rAAV5 in insect cells, cultures of Sf9 cells ($5 \times 10^6$–$1 \times 10^7$ cells per culture) were co-infected with a first baculovirus vector comprising the modified AAV5 Rep sequence, a second baculovirus vector comprising one of the modified VP sequences, and a third baculovirus comprising the ITRs and GFP sequence, each at a moi of 5. The infected Sf9 cells were cultured, lysed, and lysate fractions obtained therefrom were enriched for rAAV5 by CsCl density gradient centrifugation, using techniques described elsewhere herein. The resulting enriched lysate fractions were collected, enzymatically digested, and subjected to quantitative RT-PCR, as described above, and the number of rAAV5 vector genomes produced per Sf9 cell was determined for each of the cultures.

AAV5 VP sequences comprising SEQ ID NOS:19–22 and SEQ ID NO:24 did not support the production of significant amounts of rAAV5 genomes in Sf9 cells (i.e., less than about 1 vector genome/cell was produced). About $5 \times 10^6$ rAAV5 vector genomes were produced in Sf9 cell cultures infected with the baculovirus comprising modified AAV5 VP sequence no. 5 (comprising SEQ ID NO:23), indicating that rAAV5 genomes can be produced in insect cells in accordance with the invention.

rAAV5 produced in the Sf9 cells were substantially isolated from a portion comprising about 50% of an Sf9 cell culture infected with baculovirus comprising modified VP no.5 (comprising SEQ ID NO:23) using standard techniques. Transduction assays were performed in COS cells ($5 \times 10^5$) with the substantially isolated rAAV5 vectors obtained from this portion, as described above. About 5,000

TABLE 4

Variant regions in modified AAV5 VP sequences

| Modified VP sequence no. | VP1 start codon and nearby nucleotieds in modified sequences (differences from SEQ ID NO:17 underlined) | |
|---|---|---|
| 1 | ACCTGTAAGACGCTTTTGTTGATCACCCTCCAGATTGGTTGG | (SEQ ID NO:19) |
| 2 | GGGTGCTAAGACGGCTTTTGTTGATCACCCTCCAGATTGGTTGG | (SEQ ID NO:20) |
| 3 | GGATCCTGTTAAGACGGCTCCGTCTTTTGTTGATCACCCTCCAGATTG | (SEQ ID NO:21) |
| 4 | GCAGATCTACCTGTTAAGACGGCTCCGTCGTTTGTTGATCACCCTCCAGATTGG | (SEQ ID NO:22) |
| 5 | TAGATCTTGAACCTCTGGGCCTGGTTGAGGAACCTGCGAGACGGCTCCGTTTGTTGATCACCCTCCAGATTGGTTG | (SEQ ID NO:23) |
| 6 | TAGATCTTGAACCTCTGGGCCTGGTTGAGGAACCTGCGAGACGGCTTTTGTTGATCACCCTCCAGATTGGTTG | (SEQ ID NO:24) | of the COS cells were determined to be positive for rAAV5 transduction. This result confirms that rAAV5 vectors produced in insect cells, similar to rAAV of other serotypes produced in insect cells, are able to transduce mammalian cells.

The results of these experiments also illustrate that that by introducing a few changes in select regions of AAV Rep and VP sequences (e.g., the VP1 start codon and surrounding region), modified VP and/or Rep sequences that support improved production of AAV genomes and/or particles in insect cells can be obtained. The inventive strategy of modifying such regions can be employed to obtain suitable modified Rep and/or VP sequences for improved production of AAV genomes and particles of any suitable AAV serotype (e.g., AAV3A, AAV3B, AAV5, and AAV6) in insect cells, using techniques described herein combined with routine nucleotide sequence modification and AAV production screening experiments. For example, additional modified VP sequences suitable for the production of rAAV in insect cells can be generated by introducing other changes in the codon context of the VP1 start codon, e.g., by way of one or more nucleotide sequence substitutions, deletions, additions, or combinations thereof, with respect to a wild-type AAV VP sequence, in the region near (e.g., within about 5–20 nucleotides of) the VP1 start codon.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing an adeno-associated virus (AAV) in an insect cell, comprising:
   (i) providing at least one insect cell-compatible vector comprising
   a first nucleotide sequence comprising at least one AAV inverted terminal repeat (ITR) nucleotide sequence,
   a second nucleotide sequence comprising an open reading frame (ORF) comprising nucleotide sequences encoding AAV VP1, VP2, and VP3 capsid proteins operably linked to at least one expression control sequence for expression in an insect cell,
   a third nucleotide sequence comprising a Rep52 or a Rep40 coding sequence operably linked to at least one expression control sequence for expression in an insect cell, and
   a fourth nucleotide sequence comprising a Rep78 or a Rep68 coding sequence operably linked to at least one expression control sequence for expression in an insect cell,
   (ii) introducing said at least one insect cell-compatible vector into an insect cell, and
   (iii) maintaining said insect cell under conditions such that AAV is produced.

2. The method of claim 1, wherein said insect cell is Sf9.

3. The method of claim 1, wherein said at least one vector is a baculoviral vector, a viral vector or a plasmid.

4. The method of claim 1, wherein said vector is a baculoviral vector.

5. The method of claim 1, wherein two insect cell-compatible vectors are provided,
   a first vector comprising said first nucleotide sequence comprising at least one AAV ITR nucleotide sequence, and
   a second vector comprising said second nucleotide sequence comprising an ORF comprising nucleotide sequences encoding AAV VP1, VP2, and VP3 capsid proteins operably linked to at least one expression control sequence for expression in an insect cell, said third nucleotide sequence comprising a Rep52 or a Rep40 coding sequence operably linked to at least one expression control sequence for expression in an insect cell, and said fourth nucleotide sequence comprising a Rep78 or a Rep68 coding sequence operably linked to at least one expression control sequence for expression in an insect cell.

6. The method of claim 1, wherein three insect-compatible vectors are provided,
a first vector comprising said first nucleotide sequence comprising at least one AAV ITR nucleotide sequence,
a second vector comprising said second nucleotide sequence comprising an ORF comprising nucleotide sequences encoding AAV VP1, VP2, and VP3 capsid proteins operably linked to at least one expression control sequence for expression in an insect cell, and
a third vector comprising said third nucleotide sequence comprising a Rep52 or a Rep40 coding sequence operably linked to at least one expression control sequence for expression in an insect cell, and said fourth nucleotide sequence comprising a Rep78 or a Rep68 coding sequence operably linked to at least one expression control sequence for expression in an insect cell.

7. The method of claim 1, wherein said first nucleotide sequence further comprises at least one nucleotide sequence encoding a gene product of interest for expression in a mammalian cell and the at least one nucleotide sequence encoding a gene product of interest becomes incorporated into the genome of an AAV produced in the insect cell.

8. The method of claim 1, wherein said fourth nucleotide sequence comprises a Kozak-like expression control sequence.

9. The method of claim 1, wherein said fourth nucleotide sequence comprises an expression control sequence selected from an immediate early 1 gene (IE-1) promoter, a ΔIE-1 promoter, a promoter substantially homologous to the IE-1 promoter, and a promoter substantially homologous to the ΔIE-1 promoter.

10. The method of claim 9, wherein the ΔIE-1 promoter consists essentially of SEQ. ID. NO: 1.

11. The method of claim 1, wherein said second nucleotide sequence comprising at least one expression control sequence comprises a polyhedron (polh) promoter sequence.

12. The method of claim 1, wherein said second nucleotide sequence comprises at least one expression control sequence comprising
a nine nucleotide sequence of SEQ. ID NO: 4 or a nucleotide sequence substantially homologous to SEQ. ID NO: 4, upstream of the initiation codon of the nucleotide sequence encoding AAV VP1 capsid protein, and
a C at position 2 of the nucleotide sequence encoding AAV VP1 capsid protein.

13. The method of claim 12, wherein said second nucleotide sequence further comprises at least one modification of the nucleotide sequence encoding AAV VP1 capsid protein selected from among a G at nucleotide position 12, an A at nucleotide position 21, and a C at nucleotide position 24.

14. The method of claim 1, wherein an ACG initiation codon is an initiation codon for translation of said AAV VP1 capsid protein.

15. The method of claim 1, wherein said third nucleotide sequence encodes Rep52.

16. The method of claim 1, wherein said fourth nucleotide sequence encodes Rep78.

17. A method of producing an AAV in an insect cell, comprising:
(i) providing an insect cell comprising
a first nucleotide sequence comprising at least one AAV ITR nucleotide sequence,
a second nucleotide sequence comprising an ORF comprising nucleotide sequences encoding AAV VP1, VP2 and VP3 capsid proteins operably linked to at least one expression control sequence for expression in an insect cell,
a third nucleotide sequence comprising a Rep52 or a Rep40 coding sequence operably linked to at least one expression control sequence for expression in an insect cell,
a fourth nucleotide sequence comprising a Rep78 or a Rep68 coding sequence operably linked to at least one expression control sequence for expression in an insect cell, and, optionally,
at least one insect cell-compatible vector,
wherein at least one of the first, second, third and fourth nucleotide sequences is/are stably integrated in the insect cell and the at least one insect cell-compatible vector, when present, comprises the remainder of the first, second, third and fourth nucleotide sequences which is/are not stably integrated in the insect cell, and
(ii) maintaining the insect cell under conditions such that AAV is produced.

18. The method of claim 17, wherein said nucleotide sequence stably integrated in the insect cell is said second nucleotide sequence comprising an ORF comprising nucleotide sequences encoding AAV VP1, VP2, and VP3 capsid proteins operably linked to at least one expression control sequence for expression in an insect cell.

19. An insect cell-compatible vector comprising a nucleotide sequence encoding Rep78 or Rep68 operably linked to a ΔIE-1 promoter and a Kozak-like expression control sequence.

20. An insect cell-compatible vector comprising an ORF comprising nucleotide sequences encoding AAV VP1, VP2, and VP3 capsid proteins operably linked to at least one expression control sequence comprising:
a nine nucleotide sequence of SEQ. ID NO: 4 or a nucleotide sequence substantially homologous to SEQ. ID NO: 4, located upstream of the initiation codon of the nucleotide sequence encoding AAV VP1 capsid protein, and
a C at nucleotide position 2 of the nucleotide sequence encoding AAV VP1 capsid protein.

21. The insect cell-compatible vector of claim 20, wherein said AAV VP1, VP2, and VP3 capsid proteins are AAV2 VP1, VP2, and VP3 capsid proteins, and wherein the nucleotide sequence encoding VP1 capsid protein comprises at least one modification selected from a C at nucleotide position 12, an A at nucleotide position 21, and a C at nucleotide position 24.

22. A recombinant AAV comprising a VP1 capsid protein comprising threonine at amino acid position 1.

23. An insect cell comprising:
a first nucleotide sequence comprising at least one AAV ITR nucleotide sequence,
a second nucleotide sequence comprising an ORF comprising nucleotide sequences encoding AAV VP1, VP2, and VP3 capsid proteins operably linked to at least one expression control sequence for expression in an insect cell,
a third nucleotide sequence comprising a Rep52 or a Rep40 coding sequence operably linked to at least one expression control sequence for expression in an insect cell, and a fourth nucleotide sequence comprising a Rep78 or a Rep68 coding sequence operably linked to at least one expression control sequence for expression in an insect cell.

24. The insect cell of claim 23, wherein said fourth nucleotide sequence comprises a Kozak-like expression control sequence.

25. The insect cell of claim 23, wherein said fourth nucleotide sequence comprises an expression control sequence selected from an IE-1 promoter, a promoter substantially homologous to the IE-1 promoter, a ΔIE-1 promoter, or a promoter substantially homologous to the ΔIE-1 promoter.

26. The insect cell of claim 23, wherein said first nucleotide sequence comprises two AAV ITR nucleotide sequences and further comprises at least one nucleotide sequence encoding a gene product of interest for expression in a mammalian cell between the two AAV ITR nucleotide sequences.

27. The insect cell of claim 23, wherein at least one of said first nucleotide sequence, second nucleotide sequence, third nucleotide sequence, and fourth nucleotide sequence is stably integrated in said insect cell.

28. A method of producing an AAV in an insect cell comprising:
  (i) providing at least one insect cell-compatible vector comprising
    a first nucleotide sequence comprising at least one chimeric ITR nucleotide sequence, the ITR nucleotide sequence comprising an AAV backbone and a specific binding and a nicking site of a Rep protein from a parvovirus other than AAV,
    a second nucleotide sequence comprising an ORF comprising nucleotide sequences encoding AAV VP1, VP2, and VP3 capsid proteins operably linked to at least one expression control sequence for expression in an insect cell,
    a third nucleotide sequence comprising a Rep52 or a Rep40 coding sequence operably linked to at least one expression control sequence for expression in an insect cell, and
    a fourth nucleotide sequence comprising a nucleotide sequence encoding a parvoviral Rep protein that can specifically bind and nick the site in the ITR nucleotide sequence within the first nucleotide sequence, operably linked to at least one expression control sequence for expression in an insect cell,
  (ii) introducing said at least one insect cell-compatible vector into an insect cell, and
  (iii) maintaining said insect cell under conditions such that AAV is produced.

29. The method of claim 28, wherein said chimeric ITR nucleotide sequence comprises the specific binding and nicking site of NS-1 and said nucleotide sequence encoding a parvoviral Rep protein is that of NS-1.

30. The method of claim 7, wherein the at least one nucleotide sequence encoding a gene product of interest encodes a Rep78 or a Rep68 protein.

31. The method of claim 1, wherein said first nucleotide sequence comprises an AAV1, AAV2, or AAV4 ITR, said third nucleotide sequence comprises an AAV1, AAV2, or AAV4 Rep52 or Rep40 coding sequence, and said fourth nucleotide sequence comprises an AAV1, AAV2, or AAV4 Rep78 or Rep68 coding sequence.

32. The method of claim 1, wherein said second nucleic acid sequence encodes AAV1, AAV2, or AAV4 VP1, VP2, and VP3 capsid proteins.

33. The method of claim 1, wherein said first nucleotide sequence comprises an AAV5 ITR, said third nucleotide sequence comprises an AAV5 Rep52 or Rep40 coding sequence, and said fourth nucleotide sequence comprises an AAV5 Rep78 or Rep68 coding sequence.

34. A method of producing a parvoviral genome in an insect cell, which method comprises:
  (i) providing at least one insect cell-compatible vector comprising
    a first nucleotide sequence comprising at least one parvoviral ITR,
    a second nucleotide sequence comprising an AAV Rep52 or Rep40 coding sequence operably linked to at least one expression control sequence for expression in an insect cell, and
    a third nucleotide sequence comprising an AAV Rep78 or Rep68 coding sequence operably linked to at least one expression control sequence for expression in an insect cell,
  (ii) introducing said at least one insect cell-compatible vector into an insect cell, and
  (iii) maintaining said insect cell under conditions such that a parvovirus genome is produced therein.

35. The method of claim 34, wherein the parvovirus is a dependovirus.

36. The method of claim 35, wherein the dependovirus is a human or simian AAV.

* * * * *

SEQUENCE LISTING

```
<160> NUMBER OF SEQ ID NOS: 24

<210> SEQ ID NO 1
<211> LENGTH: 142
<212> TYPE: DNA
<213> ORGANISM: Artificial Sequence
<220> FEATURE:
<223> OTHER INFORMATION: Synthetic

<400> SEQUENCE: 1
aataaacgat aacgccgttg gtggcgtgag gcatgtaaaa ggttacatca ttatcttgtt      60
cgccatccgg ttggtataaa tagacgttca tgttggtttt tgtttcagtt gcaagttggc     120
tgcggcgcgc gcagcacctt tg                                              142

<210> SEQ ID NO 2
<211> LENGTH: 35
<212> TYPE: DNA
<213> ORGANISM: Artificial Sequence
<220> FEATURE:
<223> OTHER INFORMATION: Synthetic

<400> SEQUENCE: 2
gcgcagatct aataaacgat aacgccgttg gtggc                                 35

<210> SEQ ID NO 3
<211> LENGTH: 35
<212> TYPE: DNA
<213> ORGANISM: Artificial Sequence
<220> FEATURE:
<223> OTHER INFORMATION: Synthetic
```

-continued

```
<400> SEQUENCE: 3
gtacgcggcc gcaaaggtgc tgcgcgcgcc gcagc                                  35

<210> SEQ ID NO 4
<211> LENGTH: 9
<212> TYPE: DNA
<213> ORGANISM: Artificial Sequence
<220> FEATURE:
<223> OTHER INFORMATION: Synthetic

<400> SEQUENCE: 4 cctgttaag                                                                9

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
gttactcttc agccatggcg gggttttacg agattg                                 36

<210> SEQ ID NO 6
<211> LENGTH: 34
<212> TYPE: DNA
<213> ORGANISM: Artificial Sequence
<220> FEATURE:
<223> OTHER INFORMATION: Synthetic

<400> SEQUENCE: 6
agttactctt catcagagag agtgtcctcg agcc                                   34

<210> SEQ ID NO 7
<211> LENGTH: 49
<212> TYPE: DNA
<213> ORGANISM: Artificial Sequence
<220> FEATURE:
<223> OTHER INFORMATION: Synthetic

<400> SEQUENCE: 7
cgcggatcct gttaagacgg ctgccgacgg ttatctaccc gattggctc                   49

<210> SEQ ID NO 8
<211> LENGTH: 28
<212> TYPE: DNA
<213> ORGANISM: Artificial Sequence
<220> FEATURE:
<223> OTHER INFORMATION: Synthetic

<400> SEQUENCE: 8
gcttacagat tacgagtcag gtatctgg                                          28

<210> SEQ ID NO 9
<211> LENGTH: 50
<212> TYPE: DNA
<213> ORGANISM: Artificial Sequence
<220> FEATURE:
<223> OTHER INFORMATION: Synthetic

<400> SEQUENCE: 9
cgcggatcct gttaaagacg gctgccgacg gttatctacc cgattggctc                  50

<210> SEQ ID NO 10
<211> LENGTH: 23
```

```
<212> TYPE: DNA
<213> ORGANISM: Artificial Sequence
<220> FEATURE:
<223> OTHER INFORMATION: Synthetic

<400> SEQUENCE: 10
gcttacaggg gacgggtaag gta                                            23

<210> SEQ ID NO 11
<211> LENGTH: 7447
<212> TYPE: DNA
<213> ORGANISM: Artificial Sequence
<220> FEATURE:
<223> OTHER INFORMATION: Synthetic

<400> SEQUENCE: 11
attctctgtc acagaatgaa aattttctg tcatctcttc gttattaatg tttgtaattg      60
actgaatatc aacgcttatt tgcagcctga atggcgaatg gacgcgccc tgtagcggcg    120
cattaagcgc ggcgggtgtg gtggttacgc gcagcgtgac cgctacactt gccagcgccc    180
tagcgcccgc tcctttcgct ttcttccctt cctttctcgc cacgttcgcc ggctttcccc    240
gtcaagctct aaatcggggg ctcccttag ggttccgatt tagtgcttta cggcacctcg    300
accccaaaaa acttgattag ggtgatggtt cacgtagtgg gccatcgccc tgatagacgg    360
ttttcgccc tttgacgttg gagtccacgt tctttaatag tggactcttg ttccaaactg    420
gaacaacact caaccctatc tcggtctatt cttttgattt ataagggatt ttgccgattt    480
cggcctattg gttaaaaaat gagctgattt aacaaaaatt taacgcgaat tttaacaaaa    540
tattaacgtt tacaatttca ggtggcactt ttcggggaaa tgtgcgcgga acccctattt    600
gtttattttt ctaaatacat tcaaatatgt atccgctcat gagacaataa ccctgataaa    660
tgcttcaata atattgaaaa aggaagagta tgagtattca catttccgt gtcgccctta    720
ttccctttt tgcggcattt tgccttcctg tttttgctca cccagaaacg ctggtgaaag    780
taaagatgc tgaagatcag ttgggtgcac gagtgggtta catcgaactg gatctcaaca    840
gcggtaagat ccttgagagt tttcgccccg aagaacgttt tccaatgatg agcactttta    900
aagttctgct atgtggcgcg gtattatccc gtattgacgc cgggcaagag caactcggtc    960
gccgcataca ctattctcag aatgacttgg ttgagtactc accagtcaca gaaaagcatc   1020
ttacggatgg catgacagta agagaattat gcagtgctgc cataaccatg agtgataaca   1080
ctgcggccaa cttacttctg acaacgatcg gaggaccgaa ggagctaacc gcttttttgc   1140
acaacatggg ggatcatgta actcgccttg atcgttggga accggagctg aatgaagcca   1200
taccaaacga cgagcgtgac accacgatgc ctgtagcaat ggcaacaacg ttgcgcaaac   1260
tattaactgg cgaactactt actctagctt cccggcaaca attaatagac tggatggagg   1320
cggataaagt tgcaggacca cttctgcgct cggcccttcc ggctggctgg tttattgctg   1380
ataaatctgg agccggtgag cgtgggtctc gcggtatcat tgcagcactg gggccagatg   1440
gtaagccctc ccgtatcgta gttatctaca cgacggggag tcaggcaact atggatgaac   1500
gaaatagaca gatcgctgag ataggtgcct cactgattaa gcattggtaa ctgtcagacc   1560
aagtttactc atatatactt tagattgatt taaaacttca tttttaattt aaaaggatct   1620
aggtgaagat cctttttgat aatctcatga ccaaaatccc ttaacgtgag ttttcgttcc   1680
actgagcgtc agaccccgta gaaaagatca aaggatcttc ttgagatcct ttttttctgc   1740
gcgtaatctg ctgcttgcaa acaaaaaaac caccgctacc agcggtggtt tgtttgccgg   1800
```

-continued

```
atcaagagct accaactctt tttccgaagg taactggctt cagcagagcg cagataccaa    1860
atactgtcct tctagtgtag ccgtagttag gccaccactt caagaactct gtagcaccgc    1920
ctacatacct cgctctgcta atcctgttac cagtggctgc tgccagtggc gataagtcgt    1980
gtcttaccgg gttggactca agacgatagt taccggataa ggcgcagcgg tcgggctgaa    2040
cggggggttc gtgcacacag cccagcttgg agcgaacgac ctacaccgaa ctgagatacc    2100
tacagcgtga gcattgagaa agcgccacgc ttcccgaagg gagaaaggcg gacaggtatc    2160
cggtaagcgg cagggtcgga acaggagagc gcacgaggga gcttccaggg ggaaacgcct    2220
ggtatcttta tagtcctgtc gggtttcgcc acctctgact tgagcgtcga ttttttgtgat   2280
gctcgtcagg ggggcggagc ctatggaaaa acgccagcaa cgcggccttt ttacggttcc    2340
tggccttttg ctggcctttt gctcacatgt tctttcctgc gttatcccct gattctgtgg    2400
ataaccgtat taccgccttt gagtgagctg ataccgctcg ccgcagccga acgaccgagc    2460
gcagcgagtc agtgagcgag gaagcggaag agcgcctgat gcggtatttt ctccttacgc    2520
atctgtgcgg tatttcacac cgcagaccag ccgcgtaacc tggcaaaatc ggttacggtt    2580
gagtaataaa tggatgccct gcgtaagcgg gtgtgggcgg acaataaagt cttaaactga    2640
acaaaataga tctaaactat gacaataaag tcttaaacta gacagaatag ttgtaaactg    2700
aaatcagtcc agttatgctg tgaaaaagca tactggactt ttgttatggc taaagcaaac    2760
tcttcatttt ctgaagtgca aattgcccgt cgtattaaag aggggcgtgg ccaagggcat    2820
ggtaaagact atattcgcgg cgttgtgaca atttaccgaa caactccgcg gccgggaagc    2880
cgatctcggc ttgaacgaat tgttaggtgg cggtacttgg gtcgatatca aagtgcatca    2940
cttcttcccg tatgcccaac tttgtataga gagccactgc gggatcgtca ccgtaatctg    3000
cttgcacgta gatcacataa gcaccaagcg cgttggcctc atgcttgagg agattgatga    3060
gcgcggtggc aatgccctgc ctccggtgct cgccggagac tgcgagatca tagatataga    3120
tctcactacg cggctgctca aacctgggca gaacgtaagc cgcgagagcg ccaacaaccg    3180
cttcttggtc gaaggcagca agcgcgatga atgtcttact acggagcaag ttcccgaggt    3240
aatcggagtc cggctgatgt tgggagtagg tggctacgtc tccgaactca cgaccgaaaa    3300
gatcaagagc agcccgcatg gatttgactt ggtcagggcc gagcctacat gtgcgaatga    3360
tgcccatact tgagccacct aactttgttt tagggcgact gccctgctgc gtaacatcgt    3420
tgctgctgcg taacatcgtt gctgctccat aacatcaaac atcgacccac ggcgtaacgc    3480
gcttgctgct tggatgcccg aggcatagac tgtacaaaaa aacagtcata acaagccatg    3540
aaaaccgcca ctgcgccgtt accacgctgt cgttcggtca aggttctgga ccagttgcgt    3600
gagcgcatac gctacttgca ttacagtttta cgaaccgaac aggcttatgt caactgggtt   3660
cgtgccttca tccgtttcca cggtgtgcgt cacccggcaa ccttgggcag cagcgaagtc    3720
gaggcatttc tgtcctggct ggcgaacgag cgcaaggttt cggtctccac gcatcgtcag    3780
gcattggcgg ccttgctgtt cttctacggc aaggtgctgt gcacggatct gccctggctt    3840
caggagatcg gtagacctcg gccgtcgcgg cgcttgccgg tggtgctgac cccggatgaa    3900
gtggttcgca tcctcggttt tctggaaggc gagcatcgtt tgttcgccca ggactctagc    3960
tatagttcta gtggttggcc tacgtacccg tagtggctat ggcagggctt gccgccccga    4020
cgttggctgc gagccctggg ccttcacccg aacttggggg ttggggtggg gaaaaggaag    4080
aaacgcgggc gtattggtcc caatgggtc tcggtgggt atcgacagag tgccagccct     4140
gggaccgaac cccgcgttta tgaacaaacg acccaacacc cgtgcgtttt attctgtctt    4200
```

```
tttattgccg tcatagcgcg ggttccttcc ggtattgtct ccttccgtgt ttcagttagc    4260
ctcccccatc tcccggtacc gcatgctatg catcagctgc tagcaccatg gctcgagatc    4320
ccgggtgatc aagtcttcgt cgagtgattg taaataaaat gtaatttaca gtatagtatt    4380
ttaattaata tacaaatgat ttgataataa ttcttattta actataatat attgtgttgg    4440
gttgaattaa aggtccgtat actccggaat attaatagat catggagata attaaaatga    4500
taaccatctc gcaaataaat aagtatttta ctgttttcgt aacagttttg taataaaaaa    4560
acctataaat attccggatt attcataccg tcccaccatc gggcgcggat cctgttaaag    4620
acggctgccg acggttatct acccgattgg ctcgaggaca acctctctga gggcattcgc    4680
gagtggtggg acttgaaacc tggagccccg aagcccaaag ccaaccagca aaagcaggac    4740
gacggccggg gtctggtgct tcctggctac aagtacctcg gacccttcaa cggactcgac    4800
aagggggagc ccgtcaacgc ggcggacgca gcggccctcg agcacgacaa ggcctacgac    4860
cagcagctca aagcgggtga caatccgtac ctgcggtata accacgccga cgccgagttt    4920
caggagcgtc tgcaagaaga tacgtctttt gggggcaacc tcgggcgagc agtcttccag    4980
gccaagaagc gggttctcga acctctcggt ctggttgagg aaggcgctaa gacggctcct    5040
ggaaagaaac gtccggtaga gcagtcgcca aagagccag actcctcctc gggcatcggc    5100
aagacaggcc agcagcccgc taaaaagaga ctcaattttg gtcagactgg cgactcagag    5160
tcagtccccg atccacaacc tctcggagaa cctccagcaa ccccgctgc tgtgggacct    5220 actacaatgg cttcaggcgg tggcgcacca atggcagaca ataacgaagg cgccgacgga    5280
gtgggtaatg cctcaggaaa ttggcattgc gattccacat ggctgggcga cagagtcatc    5340
accaccagca cccgcacctg ggccttgccc acctacaata accacctcta caagcaaatc    5400
tccagtgctt caacgggggc cagcaacgac aaccactact tcggctacag cacccccctgg    5460 gggtattttg atttcaacag attccactgc cacttttcac cacgtgactg cagcgactc    5520 atcaacaaca attggggatt ccggcccaag agactcaact tcaaactctt caacatccaa    5580
gtcaaggagg tcacgacgaa tgatggcgtc acaaccatcg ctaataacct taccagcacg    5640
gttcaagtct tctcggactc ggagtaccag cttccgtacg tcctcggctc tgcgcaccag    5700
ggctgcctcc ctccgttccc ggcggacgtg ttcatgattc cgcaatacgg ctacctgacg    5760
ctcaacaatg gcagccaagc cgtgggacgt tcatccttt actgcctgga atatttccct    5820
tctcagatgc tgagaacggg caacaacttt accttcagct cacctttga ggaagtgcct    5880 ttccacagca gctacgcgca cagccagagc ctggaccggc tgatgaatcc tctcatcgac    5940
caatacctgt attcctgaa cagaactcaa atcagtccg gaagtgccca aaacaaggac    6000
ttgctgttta gccgtgggtc tccagctggc atgtctgttc agcccaaaaa ctggctacct    6060
ggaccctgtt atcggcagca gcgcgtttct aaaacaaaaa cagacaacaa caacagcaat    6120
tttacctgga ctggtgcttc aaaatataac ctcaatgggc gtgaatccat catcaaccct    6180
ggcactgcta tggcctcaca caagacgac gaagacaagt tctttcccat gagcggtgtc    6240 atgattttg gaaagagag cgccggagct tcaaacactg cattggacaa tgtcatgatt    6300
acagacgaag aggaaattaa agccactaac cctgtggcca ccgaaagatt tgggaccgtg    6360
gcagtcaatt tccagagcag cagcacagac cctgcgaccg gagatgtgca tgctatggga    6420
gcattacctg gcatggtgtg gcaagataga gacgtgtacc tgcagggtcc catttgggcc    6480
aaaattcctc acacagatgg acactttcac ccgtctcctc ttatgggcgg ctttggactc    6540
```

```
aagaacccgc ctcctcagat cctcatcaaa acacgcctg ttcctgcgaa tcctccggcg    6600
gagttttcag ctacaaagtt tgcttcattc atcacccaat actccacagg acaagtgagt    6660
gtggaaattg aatgggagct gcagaaagaa acagcaagc gctggaatcc cgaagtgcag     6720
tacacatcca attatgcaaa atctgccaac gttgatttta ctgtggacaa caatggactt    6780
tatactgagc ctcgccccat tggcacccgt taccttaccc gtcccctgta agcttcccgc    6840
ttaaggtcgt gtgaccgccg gcaatgatca cgcggccgct ttcgaatcta gagcctgcag    6900
tctcgacaag cttgtcgaga agtactagag gatcataatc agccatacca catttgtaga    6960
ggttttactt gctttaaaaa acctcccaca cctcccctg aacctgaaac ataaaatgaa     7020
tgcaattgtt gttgttaact tgtttattgc agcttataat ggttacaaat aaagcaatag    7080
catcacaaat ttcacaaata aagcattttt ttcactgcat tctagttgtg gtttgtccaa    7140
actcatcaat gtatcttatc atgtctggat ctgatcactg cttgagccta ggagatccga    7200
accagataag tgaaatctag ttccaaacta ttttgtcatt tttaattttc gtattagctt    7260
acgacgctac acccagttcc catctatttt gtcactcttc cctaaataat ccttaaaaac    7320
tccatttcca ccctcccag ttcccaacta ttttgtccgc ccacagcggg gcattttct      7380 tcctgttatg tttttaatca aacatcctgc caactccatg tgacaaaccg tcatcttcgg    7440
ctactt                                                               7447
```

<210> SEQ ID NO 12
<211> LENGTH: 42
<212> TYPE: DNA
<213> ORGANISM: Artificial Sequence
<220> FEATURE:
<223> OTHER INFORMATION: Synthetic

<400> SEQUENCE: 12

```
cggatcctgt taagacggct gacggttacc ttccagattg gc                       42
```

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13

```
gttattacag gtgggtgagg tagcg                                          25
```

<210> SEQ ID NO 14
<211> LENGTH: 7744
<212> TYPE: DNA
<213> ORGANISM: Artificial Sequence
<220> FEATURE:
<223> OTHER INFORMATION: Synthetic

<400> SEQUENCE: 14

```
ttctctgtca cagaatgaaa attttctgt catctcttcg ttattaatgt ttgtaattga     60
ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcggggc tcccttagg gttccgattt agtgctttac ggcacctcga    300
ccccaaaaaa cttgattagg gtgatggttc acgtagtggg ccatcgccct gatagacggt    360
ttttcgccct tgacgttgg agtccacgtt ctttaatagt ggactcttgt tccaaactgg    420
```

-continued

```
aacaacactc aaccctatct cggtctattc ttttgattta aagggatttt tgccgatttc   480
ggcctattgg ttaaaaaatg agctgattta acaaaaattt aacgcgaatt ttaacaaaat   540
attaacgttt acaatttcag gtggcacttt tcggggaaat gtgcgcggaa cccctatttg   600
tttatttttc taaatacatt caaatatgta tccgctcatg agacaataac cctgataaat   660
gcttcaataa tattgaaaaa ggaagagtat gagtattcaa catttccgtg tcgcccttat   720
tcccttttt gcggcatttt gccttcctgt ttttgctcac ccagaaacgc tggtgaaagt   780
aaaagatgct gaagatcagt tgggtgcacg agtgggttac atcgaactgg atctcaacag   840
cggtaagatc cttgagagtt ttcgccccga agaacgtttt ccaatgatga gcacttttaa   900
agttctgcta tgtggcgcgg tattatcccg tattgacgcc gggcaagagc aactcggtcg   960
ccgcatacac tattctcaga atgacttggt tgagtactca ccagtcacag aaaagcatct  1020
tacggatggc atgacagtaa gagaattatg cagtgctgcc ataaccatga gtgataacac  1080
tgcggccaac ttacttctga caacgatcgg aggaccgaag gagctaaccg cttttttgca  1140
caacatgggg gatcatgtaa ctcgccttga tcgttgggaa ccggagctga atgaagccat  1200
accaaacgac gagcgtgaca ccacgatgcc tgtagcaatg gcaacaacgt tgcgcaaact  1260
attaactggc gaactactta ctctagcttc ccggcaacaa ttaatagact ggatggaggc  1320
ggataaagtt gcaggaccac ttctgcgctc ggcccttccg gctggctggt ttattgctga  1380
taaatctgga gccggtgagc gtgggtctcg cggtatcatt gcagcactgg ggccagatgg  1440
taagccctcc cgtatcgtag ttatctacac gacggggagt caggcaacta tggatgaacg  1500
aaatagacag atcgctgaga taggtgcctc actgattaag cattggtaac tgtcagacca  1560
agtttactca tatatacttt agattgattt aaaacttcat ttttaattta aaaggatcta  1620
ggtgaagatc ctttttgata atctcatgac caaaatccct taacgtgagt tttcgttcca  1680
ctgagcgtca gaccccgtag aaaagatcaa aggatcttct tgagatcctt ttttttctgcg  1740
cgtaatctgc tgcttgcaaa caaaaaaacc accgctacca gcggtggttt gtttgccgga  1800
tcaagagcta ccaactcttt ttccgaaggt aactggcttc agcagagcgc agataccaaa  1860
tactgtcctt ctagtgtagc cgtagttagg ccaccacttc aagaactctg tagcaccgcc  1920
tacatacctc gctctgctaa tcctgttacc agtggctgct gccagtggcg ataagtcgtg  1980
tcttaccggg ttggactcaa gacgatagtt accggataag cgcagcggt cgggctgaac  2040
ggggggttcg tgcacacagc ccagcttgga gcgaacgacc tacaccgaac tgagatacct  2100
acagcgtgag cattgagaaa gcgccacgct tcccgaaggg agaaaggcgg acaggtatcc  2160
ggtaagcggc agggtcggaa caggagagcg cacgagggag cttccagggg gaaacgcctg  2220
gtatctttat agtcctgtcg ggtttcgcca cctctgactt gagcgtcgat ttttgtgatg  2280
ctcgtcaggg gggcggagcc tatggaaaaa cgccagcaac gcggcctttt tacggttcct  2340
ggccttttgc tggccttttg ctcacatgtt ctttcctgcg ttatccctg attctgtgga  2400
taaccgtatt accgcctttg agtgagctga taccgctcgc cgcagccgaa cgaccgagcg  2460
cagcgagtca gtgagcgagg aagcggaaga gcgcctgatg cggtattttc tccttacgca  2520
tctgtgcggt atttcacacc gcagaccagc cgcgtaacct ggcaaaatcg gttacggttg  2580
agtaataaat ggatgccctg cgtaagcggg tgtgggcgga caataaagtc ttaaactgaa  2640
caaaatagat ctaaactatg acaataaagt cttaaactag acagaatagt tgtaaactga  2700
aatcagtcca gttatgctgt gaaaaagcat actggacttt tgttatggct aaagcaaact  2760
```

-continued

| | | |
|---|---|---|
| cttcattttc tgaagtgcaa attgcccgtc gtattaaaga ggggcgtggc caagggcatg | 2820 |
| gtaaagacta tattcgcggc gttgtgacaa tttaccgaac aactccgcgg ccgggaagcc | 2880 |
| gatctcggct tgaacgaatt gttaggtggc ggtacttggg tcgatatcaa agtgcatcac | 2940 |
| ttcttcccgt atgcccaact tgtatagag agccactgcg ggatcgtcac cgtaatctgc | 3000 |
| ttgcacgtag atcacataag caccaagcgc gttggcctca tgcttgagga gattgatgag | 3060 |
| cgcggtggca atgccctgcc tccggtgctc gccggagact gcgagatcat agatatagat | 3120 |
| ctcactacgc ggctgctcaa acctgggcag aacgtaagcc gcgagagcgc caacaaccgc | 3180 |
| ttcttggtcg aaggcagcaa gcgcgatgaa tgtcttacta cggagcaagt tcccgaggta | 3240 |
| atcggagtcc ggctgatgtt gggagtaggt ggctacgtct ccgaactcac gaccgaaaag | 3300 |
| atcaagagca gcccgcatgg atttgacttg gtcagggccg agcctacatg tgcgaatgat | 3360 |
| gcccatactt gagccaccta actttgtttt agggcgactg ccctgctgcg taacatcgtt | 3420 |
| gctgctgcgt aacatcgttg ctgctccata acatcaaaca tcgacccacg gcgtaacgcg | 3480 |
| cttgctgctt ggatgcccga ggcatagact gtacaaaaaa acagtcataa caagccatga | 3540 |
| aaaccgccac tgcgccgtta ccaccgctgc gttcggtcaa ggttctggac cagttgcgtg | 3600 |
| agcgcatacg ctacttgcat tacagtttac gaaccgaaca ggcttatgtc aactgggttc | 3660 |
| gtgccttcat ccgtttccac ggtgtgcgtc acccggcaac cttgggcagc agcgaagtcg | 3720 |
| aggcatttct gtcctggctg gcgaacgagc gcaaggtttc ggtctccacg catcgtcagg | 3780 |
| cattggcggc cttgctgttc ttctacgca aggtgctgtg cacggatctg ccctggcttc | 3840 |
| aggagatcgg tagacctcgg ccgtcgcggc gcttgccggt ggtgctgacc ccggatgaag | 3900 |
| tggttcgcat cctcggtttt ctggaaggcg agcatcgttt gttcgcccag gactctagct | 3960 |
| atagttctag tggttggcct acgtacccgt agtggctatg gcagggcttg ccgccccgac | 4020 |
| gttggctgcg agccctgggc cttcacccga acttgggggt tggggtgggg aaaaggaaga | 4080 |
| aacgcgggcg tattggtccc aatgggtct cggtggggta tcgacagagt gccagccctg | 4140 |
| ggaccgaacc ccgcgtttat gaacaaacga cccaacaccc gtgcgtttta ttctgtcttt | 4200 |
| ttattgccgt catagcgcgg gttccttccg gtattgtctc cttccgtgtt tcagttagcc | 4260 |
| tcccccatct cccggtaccg catgctatgc atcagctgct agcaccatgg ctcgagatcc | 4320 |
| cgggtgatca agtcttcgtc gagtgattgt aaataaaatg taatttacag tatagtatt | 4380 |
| taattaatat acaaatgatt tgataataat tcttatttaa ctataatata ttgtgttggg | 4440 |
| ttgaattaaa ggtccgtata ctccggaata ttaatagatc atggagataa ttaaaatgat | 4500 |
| aaccatctcg caaataaata agtattttac tgttttcgta acagttttgt aataaaaaaa | 4560 |
| cctataaata ttccggatta ttcataccgt cccaccatcg ggcgcggatc ctgttaaaga | 4620 |
| cggctgccga cggttatcta cccgattggc tcgaggacaa cctctctgaa ggcgttcgag | 4680 |
| agtggtgggc gctgcaacct ggagccccta aacccaaggc aaatcaacaa catcaggaca | 4740 |
| acgctcgggg tcttgtgctt ccgggttaca aatacctcgg acccgcaac ggactcgaca | 4800 |
| aggggggaacc cgtcaacgca gcggacgcgg cagccctcga gcacgacaag gcctacgacc | 4860 |
| agcagctcaa ggccggtgac aaccctacc tcaagtacaa ccacgccgac gcggagttcc | 4920 |
| agcagcggct tcagggcgac acatcgtttg ggggcaacct cggcagagca gtcttccagg | 4980 |
| ccaaaaagag ggttcttgaa cctcttggtc tggttgagca agcgggtgag acggctcctg | 5040 |
| gaaagaagag accgttgatt gaatccccc agcagcccga ctcctccacg ggtatcggca | 5100 |
| aaaaaggcaa gcagccggct aaaaagaagc tcgttttcga agacgaaact ggagcaggcg | 5160 |

```
acggaccccc tgagggatca acttccggag ccatgtctga tgacagtgag atgcgtgcag    5220
cagctggcgg agctgcagtc gagggcggac aaggtgccga tggagtgggt aatgcctcgg    5280
gtgattggca ttgcgattcc acctggtctg agggccacgt cacgaccacc agcaccagaa    5340
cctgggtctt gcccacctac aacaaccacc tctacaagcg actcggagag agcctgcagt    5400
ccaacaccta caacggattc tccaccccct ggggatactt tgacttcaac cgcttccact    5460
gccacttctc accacgtgac tggcagcgac tcatcaacaa caactggggc atgcgaccca    5520
aagccatgcg ggtcaaaatc ttcaacatcc aggtcaagga ggtcacgacg tcgaacggcg    5580
agacaacggt ggctaataac cttaccagca cggttcagat ctttgcggac tcgtcgtacg    5640
aactgccgta cgtgatggat gcgggtcaag agggcagcct gcctcctttt cccaacgacg    5700
tctttatggt gccccagtac ggctactgtg actggtgac cggcaacact tcgcagcaac     5760
agactgacag aaatgccttc tactgcctgg agtactttcc ttcgcagatg ctgcggactg    5820
gcaacaactt tgaaattacg tacagttttg agaaggtgcc tttccactcg atgtacgcgc    5880
acagccagag cctggaccgg ctgatgaacc ctctcatcga ccagtacctg tggggactgc    5940
aatcgaccac caccggaacc accctgaatg ccgggactgc caccaccaac tttaccaagc    6000
tgcggcctac caacttttcc aactttaaaa agaactggct gcccgggcct tcaatcaagc    6060
agcagggctt ctcaaagact gccaatcaaa actacaagat ccctgccacc gggtcagaca    6120
gtctcatcaa atacgagacg cacagcactc tggacgaag atggagtgcc ctgaccccg      6180 gacctccaat ggccacggct ggacctgcgg acagcaagtt cagcaacagc cagctcatct    6240
ttgcggggcc taaacagaac ggcaacacg ccaccgtacc cgggactctg atcttcacct     6300
ctgaggagga gctggcagcc accaacgcca ccgatacgga catgtggggc aacctacctg    6360
gcggtgacca gagcaacagc aacctgccga ccgtggacag actgcagacc ttgggagccg    6420
tgcctggaat ggtctggcaa acagagaca tttactacca gggtcccatt tgggccaaga     6480
ttcctcatac cgatggacac tttcaccct caccgctgat tggtgggttt gggctgaaac     6540
acccgcctcc tcaaattttt atcaagaaca ccccggtacc tgcgaatcct gcaacgacct    6600
tcagctctac tccggtaaac tccttcatta ctcagtacag cactggccag gtgtcggtgc    6660
agattgactg ggagatccag aaggagcggt ccaaacgctg gaaccccgag gtccagttta    6720
cctccaacta cggacagcaa aactctctgt tgtgggctcc cgatgcggct gggaaataca    6780
ctgagcctag ggctatcggt acccgctacc tcacccacca cctgtaataa cctgttaatc    6840
aataaaccgg tttattcgtt tcagttgaac tttggtctcc gtgtccttct tatcttatct    6900
cgtttccatg gctactgcgt acataagcag cggcctgcgg cgcttgcgct tcgcggttta    6960
caactgccgg ttaatcagta acttctggca aaccagatga tggagttggc cacattagct    7020
atgcgcgctc gctcactcac tcggccctgg agaccaaagg tctccagact gccggcctct    7080
ggccggcagg gccgagtgag tgagcgagcg cgcatagagg gagtggccaa ttcccgctta    7140
aggtcgtgtg accgccggca atgatcacgc ggccgctttc gaatctagag cctgcagtct    7200
cgacaagctt gtcgagaagt actagaggat cataatcagc cataccacat tgtagaggt     7260 tttacttgct ttaaaaaacc tcccacacct cccctgaacc tgaaacata aaatgaatgc      7320 aattgttgtt gttaacttgt ttattgcagc ttataatggt tacaaataaa gcaatagcat    7380
cacaaatttc acaaataaag catttttttc actgcattct agttgtggtt tgtccaaact    7440
catcaatgta tcttatcatg tctggatctg atcactgctt gagcctagga gatccgaacc    7500
```

```
agataagtga aatctagttc caaactattt tgtcattttt aattttcgta ttagcttacg    7560
acgctacacc cagttcccat ctattttgtc actcttccct aaataatcct taaaaactcc    7620
atttccaccc ctcccagttc ccaactattt tgtccgccca cagcggggca tttttcttcc    7680
tgttatgttt ttaatcaaac atcctgccaa ctccatgtga caaaccgtca tcttcggcta    7740
cttt                                                                 7744
```

```
<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
cagatctatg gctaccttct atgaagtcat tgttcg                               36
```

```
<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
ggacatggcg ctcgtcaact ggctcgtgga gcacg                                35
```

```
<210> SEQ ID NO 17
<211> LENGTH: 32
<212> TYPE: DNA
<213> ORGANISM: Artificial Sequence
<220> FEATURE:
<223> OTHER INFORMATION: Synthetic

<400> SEQUENCE: 17
ttatcaccaa cttcttccaa ccaatctgga gg                                   32
```

```
<210> SEQ ID NO 18
<211> LENGTH: 31
<212> TYPE: DNA
<213> ORGANISM: adeno-associated virus serotype 5

<400> SEQUENCE: 18
atgtcttttg ttgatcaccc tccagattgg t                                    31
```

```
<210> SEQ ID NO 19
<211> LENGTH: 43
<212> TYPE: DNA
<213> ORGANISM: Artificial Sequence
<220> FEATURE:
<223> OTHER INFORMATION: Synthetic

<400> SEQUENCE: 19
acctgtaaga cggcttttgt tgatcaccct ccagattggt tgg                       43
```

```
<210> SEQ ID NO 20
<211> LENGTH: 44
<212> TYPE: DNA
<213> ORGANISM: Artificial Sequence
<220> FEATURE:
<223> OTHER INFORMATION: Synthetic

<400> SEQUENCE: 20
gggtgctaag acggcttttg ttgatcaccc tccagattgg ttgg                      44
```

```
<210> SEQ ID NO 21
<211> LENGTH: 48
<212> TYPE: DNA
<213> ORGANISM: Artificial Sequence
<220> FEATURE:
<223> OTHER INFORMATION: Synthetic

<400> SEQUENCE: 21
ggatcctgtt aagacggctc cgtcttttgt tgatcaccct ccagattg                    48

<210> SEQ ID NO 22
<211> LENGTH: 54
<212> TYPE: DNA
<213> ORGANISM: Artificial Sequence
<220> FEATURE:
<223> OTHER INFORMATION: Synthetic

<400> SEQUENCE: 22
gcagatctac ctgttaagac ggctccgtcg tttgttgatc accctccaga ttgg             54

<210> SEQ ID NO 23
<211> LENGTH: 76
<212> TYPE: DNA
<213> ORGANISM: Artificial Sequence
<220> FEATURE:
<223> OTHER INFORMATION: Synthetic

<400> SEQUENCE: 23
tagatcttga acctctgggc ctggttgagg aacctgcgag acggctccgt tgttgatca        60 ccctccagat tggttg                                                      76

<210> SEQ ID NO 24
<211> LENGTH: 73
<212> TYPE: DNA
<213> ORGANISM: Artificial Sequence
<220> FEATURE:
<223> OTHER INFORMATION: Synthetic

<400> SEQUENCE: 24
tagatcttga acctctgggc ctggttgagg aacctgcgag acggcttttg ttgatcaccc       60
tccagattgg ttg                                                         73
```